United States Patent [19]
Hou et al.

[11] Patent Number: 4,663,163
[45] Date of Patent: May 5, 1987

[54] MODIFIED POLYSACCHARIDE SUPPORTS

[76] Inventors: Kenneth C. Hou, 14 Hunting Ridge Rd., S. Glastonbury, Conn. 06073; Tung-Ping D. Liao, 109 Vernwood Dr., Vernon, Conn. 06066

[21] Appl. No.: 576,448

[22] Filed: Feb. 2, 1984

Related U.S. Application Data

[63] Continuation-in-part of Ser. No. 466,114, Feb. 14, 1983, abandoned.

[51] Int. Cl.$^4$ .................. A61K 35/16; B01J 20/00
[52] U.S. Cl. .................................. 424/101; 424/78; 424/85; 424/88; 424/483; 435/174; 435/178; 435/179; 435/180; 435/181; 435/182; 502/402; 502/403; 502/404; 527/300; 527/312; 527/313; 527/315
[58] Field of Search ............... 527/300, 312, 313, 315; 435/178, 179; 502/402, 403, 404; 424/101

[56] References Cited

U.S. PATENT DOCUMENTS

| | | |
|---|---|---|
| 3,251,475 | 5/1966 | Till et al. . |
| 3,311,608 | 3/1967 | Murphy . |
| 3,338,883 | 8/1967 | Tesoro et al. . |
| 3,380,799 | 4/1968 | Elizer et al. . |
| 3,455,853 | 7/1969 | Dekking et al. ............ 527/312 |
| 3,562,289 | 2/1971 | Batista et al. . |
| 3,651,210 | 3/1972 | Shepler et al. . |
| 3,885,069 | 5/1975 | Roberts et al. . |
| 3,985,616 | 10/1976 | Weaver et al. . |
| 4,028,290 | 6/1977 | Reid ............................ 527/312 |
| 4,038,140 | 7/1977 | Jaworek et al. . |
| 4,070,348 | 1/1978 | Kraemer et al. . |
| 4,102,746 | 7/1978 | Goldberg . |
| 4,134,863 | 1/1979 | Fanta et al. . |
| 4,144,190 | 3/1979 | Bowes et al. ............... 502/402 |
| 4,198,326 | 4/1980 | Lishevsaya . |
| 4,256,613 | 3/1981 | Franks et al. . |
| 4,262,108 | 4/1981 | Blount . |
| 4,264,766 | 4/1981 | Fischer . |
| 4,281,233 | 7/1981 | Coupek . |
| 4,384,957 | 5/1983 | Crowder . |
| 4,400,496 | 8/1983 | Butler et al. ............... 527/313 |
| 4,412,000 | 10/1983 | Lehmann et al. . |
| 4,436,813 | 3/1984 | Wood et al. ............... 435/179 |
| 4,501,871 | 2/1985 | Bartl et al. ................. 527/313 |

FOREIGN PATENT DOCUMENTS

| | | |
|---|---|---|
| 2273816 | 1/1976 | France . |
| 2293914 | 7/1976 | France . |
| 1157300 | 5/1967 | United Kingdom . |

Primary Examiner—Sam Rosen
Attorney, Agent, or Firm—Michael E. Zall; Jorge Goldstein; Sam Fox

[57] ABSTRACT

A modified polysaccharide material which comprises: (1) polysaccharide covalently bonded to a synthetic polymer; (2) the synthetic polymer being made from (a) a polymerizable compound which is capable of being covalently coupled directly or indirectly to said polysaccharide, and (b) one or more polymerizable compounds containing (i) an ionizable chemcial group, (ii) a chemical group capable of transformation to an ionizable chemical group, (iii) a chemical group capable of causing the covalent coupling of the compound (b) to an affinity ligand or a biologically active molecule or (iv) a hydrophobic compound.

26 Claims, 7 Drawing Figures

MODIFIED POLYSACCHARIDE SUPPORTS

The present application is a continuation-in-part of application Ser. No. 466,114, filed Feb. 14, 1983, now abandoned.

BACKGROUND OF THE INVENTION

1. Field of the Invention

The present invention relates to carrier supports such as chromatographic supports, and methods for their preparation and use.

2. Brief Description of the Background Art

The broad applicability of ion exchange chromatography, which ranges from separation of inorganic and organic ions to that of protein molecules and other biomolecules, has made it a powerful and versatile tool for chemical and biochemical separations. The technique was originally limited to the use of natural products such as cellulose, clay and other minerals containing mobile ions that would exchange with ionic materials in the surrounding solute phase. Because of the low exchange capacity of these natural products, however, practical utilization thereof was limited, and synthetic organic polymers capable of exchanging ions were developed.

Among the first generation of synthetic ion exchange materials were the ion exchange resins. The fundamental framework of these ion exchange resins is an elastic three-dimensional hydrocarbon network comprising ionizable groups, either cationic or anionic, chemically bonded to the backbone of a hydrocarbon framework. The network is normally fixed, insoluble in common solvents and is chemically inert. The ionizable functional groups attached to the matrix carry active ions which can react with or can be replaced by ions in the solute phase. Therefore, the ions in the solute phase can be easily exchanged for the ions initially bound to the polymeric resins. Typical examples of commercially available ion exchange resins are the polystyrenes cross-linked with DVB (divinylbenzene), and the methacrylates copolymerized with DVB. In the case of polystyrene, a three-dimensional network is formed first, and the functional groups are then introduced into benzene rings through chloromethylation. Since ion exchange resins are elastic three-dimensional polymers, they have no definite pore size; only a steadily increasing resistance of the polymer network limits the uptake of ions and molecules of increasing size.

The resistance to flow exhibited by these resins is controlled by the degree of crosslinking. With a low degree of crosslinking, the hydrocarbon network is more easily stretched, the swelling is large, and the resin exchanges small ions rapidly and even permits relatively large ions to undergo reaction. Conversely, as the crosslinking is increased, the hydrocarbon matrix is less resilient, the pores of the resin network are narrowed, the exchange process is slower, and the exchanger increases its tendency to exclude large ions from entering the structure. The ion exchange resins made from polymeric resins have been successfully applied for the removal of both organic and inorganic ions from aqueous media but they are normally unsuitable for the separation of biopolymers such as proteins. This is due, among others, to the following reasons:

(1) The highly crosslinked structure of the resins has rather narrow pores to accommodate the diffusion of proteins; the proteins therefore are virtually restricted to the macrosurface area of the beads with consequent limitation of solute loadings;

(2) The high charge density close to the proximity of the resin surface is unsuitable, since it causes excessive binding and distortion of protein structure;

(3) The hydrocarbon matrix is usually hydrophobic and is potentially dangerous to the subtle three-dimensional structure of biopolymers, often causing denaturation of proteins.

The next generation of chromatographic materials useful for separation of proteins and other labile biological substances was based on cellulose ion exchangers. These lacked nonspecific adsorption and had practicable pore structure. Such prior art ion exchange celluloses are made by attaching substituent groups with either basic or acidic properties to the cellulose molecule by esterification, etherification, or oxidation reactions. Examples of cationic exchange celluloses are carboxymethylated cellulose (CM), succinic half esters of cellulose, sulfoethylated cellulose, and phosphorylated cellulose. Examples of anionic exchange celluloses are diethylaminoethyl cellulose (DEAE), and triethylaminoethyl cellulose (TEAE). Ion exchange materials based on cellulose as the principal backbone or anchoring polymer, however, have not enjoyed complete success due primarily to an inherent property of cellulose: its affinity for water. Thus, prior art ion exchange materials based on cellulose, while typically having high exchange capacity, are difficult to use as a consequence of their tendency to swell, gelatinize or disperse on contact with an aqueous solution. An ideal ion exchange material should minimally interact with the solvent system which carries the ions in solution through its pores; only in this manner is it possible to obtain a rapid, free flowing ion exchange system.

A third generation of ion exchange materials, which were developed to solve some of these problems, were the ion exchange gels. There gels comprise large pore gel structures and include the commercially known material Sephadex ®, which is a modified dextran. The dextran chains are crosslinked to give a three-dimensional polymeric network. The functional groups are attached by either linkages to the glucose units of the dextran chains. Proteins are not denatured by the hydrophilic polymeric network. Sephadex ® exhibits very low nonspecific adsorption, which makes it ideal as a matrix for biological separations. However, the porosity of ion exchange gels is critically dependent on its swelling properties, which in turn is affected by the environmental ionic strength, pH and the nature of the counter-ions. Swelling of gels in buffer is caused primarily by the tendency of the functional groups to become hydrated. The amount of swelling is directly proportional to the number of hydrophilic functional groups attached to the gel matrix, and is inversely proportional to the degree of crosslinking present in the gel. This characteristic swelling is a reversible process, and at equilibrium there is a balance between two forces: (1) the tendency of the gel to undergo further hydration, and hence to increase the osmotic pressure within the gel beads, and (2) the elastic forces of the gel matrix. The osmotic pressure is attributed almost entirely to the hydration of the functional groups, and, since different ions have different degrees of hydration, the particular counter ions in an ion exchange gel can be expected to have a considerable influence upon the degree of swelling. Since the pH, the electrolyte concentration and the nature of the counter-ion can all affect the hydration, leading to a different degree of gel swelling, the pore size in the gels is not in well defined form but is rather dependent on the environmental conditions. Gels without crosslinking provide large pores and high capacity due to maximum swelling. They suffer, however, from the weakness of structure integrity and can easily be crushed with a minimum amount of pressure. Removal of the solvent from the gels often results in collapse of the matrix. Highly crosslinked gels have mechanical strength, but lose capacity and pore size due to restrictions in swelling.

Ion exchange gels made from synthetic polymers have also been used, and they include crosslinked polyacrylamide (Bio-Gel P ®), microreticular forms of polystyrene (Styragel ®), poly(vinyl acetate) (Merck-o-Gel OR ®), crosslinked poly(2-hydroxy ethylmethacrylate)(Spheron ®), and polyacryloylmorpholine (Enzacryl ®). All of these follow the general trend: it may be possible to obtain dimensional stability with high flow rate or, alternatively, high capacity with swelling. It is, however, not possible to obtain both capacity and high flow rate at the same time.

The failure of single components to have both capacity and dimensional stability led to yet another generation of ion exchange materials comprising composite structures, e.g., hybrid gels. Hybrid gels are made by combining a semi-rigid component, for the purpose of conferring mechanical stability, with a second component, a softer network, which is responsible for carrying functional groups. Agarose gel, which would otherwise be very soft and compressible, can be made stronger through hydridizing with cross-linked polyacrylamide. The crosslinked polyacrylamide component is mechanically stronger than the agarose, improves the gel flow properties, and reduces the gel swelling, but it sacrifices molecular fractionation range. Examples of hybrid gels other than polyacrylamide/agarose (Ultrogels ®), are polyacryloylmorpholine and agarose (Enzacryl ®), and composite polystyrenes with large pore polystyrenes as a framework filled with a second type of lightly cross-linked polymer.

Yet another composite gel structure is achieved by combining inorganic materials coated with organics, and are the types known as Spherosil ®. Porous silica beds are impregnated with DEAE dextran so that the product will have the mechanical properties of silica, with the ion exchange properties of DEAE dextrans. These composites, however, have severe channeling defects arising out of particle packing, and they have capacity limitations on the coated surfaces.

Totally rigid inorganic supports such as porous silica or porous glass which are not susceptible to degradation have also been used to provide high porosity, and high flow rate systems. The major problem, however, is nonspecific adsorption of proteins due to the silanol groups on the silica surface. Since the hydrolysis of silica is directly related to the pH conditions, the nonspecific adsorption by silica is minimal at neutral pH, but increases as the pH changes both to the acidic and alkaline ranges. A monolayer coating by either hydrophilic organic polymers or silanization has been used in an attempt to overcome this problem.

In the technique of affinity chromatography, which enables the efficient isolation of biological macromolecules or biopolymers, by utilizing their recognition sites for certain supported chemical structures with a high degree of selectivity, the prior art has also utilized materials of varying chemical structure as supports. For example, agarose gels and crosslinked agarose gels have been the most widely used support materials. Their hydrophilicity makes them relatively free of nonspecific binding, but their compressibility make them less attractive as carriers in large scale processing, such as in manufacturing. Controlled-pore glass (CPG) beads have also been used in affinity chromatography. Although high throughputs can be obtained with columns packed with CPG, this carrier is even more expensive than agarose gel beads. Cellulose particles have also been used by immunochemists for synthetic affinity sorbents. However, compared to agarose gels, cellulose particles are formed with more difficulty and therefore, have received less attention in the preparation of affinity sorbents for enzymes. Cellulose, however, is perhaps the least expensive of all-support matrices. Two lesser used support matrices are polyacrylamide gel beads and Sephadex ® gel beads made from dextran and epichlorohydrin. Although convenient methods have been developed for using them, the softness of these beads yields poor column packings, and their low molecular porosity yields a sorbent with poor ligand availability to the ligate.

Coupek et al., U.S. Pat. No. 4,281,233 show supports for affinity chromatography which comprise copolymers of hydroxy alkyl acrylates or methacrylates with cross-linking monomers. The copolymers contain covalently attached mono- or oligosaccharides (An oligosaccharide is defined in the art as having up to nine saccharide units. See, e.g., Roberts, J. D., and Caserio, M. C., *Basic Principles of Organic Chemistry*, 1964, p. 615.)

A carrier to bio-active materials is also disclosed in Nakashima et al., U.S. Pat. No. 4,352,884. The Nakashima carrier comprises a substrate coated with a copolymer. The substrate may be one of various materials, including inorganic materials such as glass, silica, alumina, synthetic high polymers such as polystyrene, polyethylene and the like, and naturally occurring high polymers such as cellulose. The copolymer is made of a hydrophilic acrylate or methacrylate monomer which is a hydroxy or alkoxy alkyl acrylate or methacrylate, and a copolymerizable unsaturated carboxylic acid or amine. The base material or substrate is coated with the copolymer by conventional coating or deposition procedures, such as spraying, dipping, phase separation or the like. The copolymer may also contain small amounts of a cross-linking agent such as glycidyl acrylate or methacrylate. The crosslinking agent allows for cross-linking treatment after the coating process, and provides for the prevention of elution (presumably of the bioactive materials) from the coating layer. The amounts of cross-linking agent are quite small, and range between 0.5 and 1 percent by weight of the total copolymer weight. Such amounts of cross-linking agent are insufficient to cause substantial covalent bonding or grafting of the copolymer onto the underlying substrate. The copolymer in Nakashima is thus essentially only physically coating the underlying substrate. Physical coating, however, is accompanied by a series of problems. The carrier would not be expected to have an even distribution of the copolymer, would show a multilayered structure, and may have a possible uneven distribution of functional groups.

Another reference of interest is Kraemer, U.S. Pat. No. 4,070,348, which shows copolymers of glycidyl- and amino-containing acrylates, useful as carriers for biologically active substances, such as polysaccharides, enzymes, peptides, hormones, etc. The structure of the final product in Kraemer is that of an acrylic copolymer chain covalently modified at a multiplicity of sites thereon with substances such as enzymes, proteins, and the like.

This review of the prior art, its advantages and drawbacks, leads to the conclusion that there exists a need for a support useful both for ion exchange and affinity chromatography-based purification which will have high stability, high porosity, low nonspecific adsorption, high flow rate, poor compressibility, controlled gelation, and which will be useful for industrial-scale biological separations. It is the industrial level of manufacturing, especially, where the aforementioned drawbacks have had their most important effect and where this need is the strongest.

Industrial scale molecular separation materials comprising fibrous matrices with particulate immobilized therein have been described in commonly assigned copending U.S. patent application Ser. No. 287,609 by Crowder, filed in the U.S. Patent and Trademark Office on July 28, 1981, now U.S. Pat. No. 4,384,957, which is herein incorporated by reference. This application describes a composite fiber material formed by wet laying a sheet from an aqueous slurry of particulate, small refined fiber pulp and long soft fiber pulp. The purpose of the soft long fiber is to physically hold clumps of particulate material and refined pulp together. Sheets are formed from a wet slurry by vacuum filtration, wherein the long fibers form in a plane which is perpendicular to the direction of flow of the chromatographic carrier fluid. This permits channels to form in the composite material which are perpendicular to the direction of flow of the chromatographic carrier fluid. This permits channels to form in the composite material, which are perpendicular to the direction of flow, and allows these materials to serve as internal flow distributors. The resulting matrix structure has proven to be an effective way of eliminating channeling defects through internal flow distribution mechanisms.

Using a fibrous/particulate matrix with addition of cationic polymers to the slurry and crosslinking the polymers to the matrices by oven drying has yielded a filtration matrix with a positive charge coated on the surface thereof. Such charged matrices can be used for filtering minute amounts of impurities from large volumes of liquid by adsorption. (See, for example Ostreicher, U.S. Pat. Nos. 4,007,113 and 4,007,114, as well as U.S. Pat. Nos. 4,305,782 and 4,309,247, which are all herein incorporated by reference.)

It is inevitable in prior art wet slurrying processes with slurries comprising cationic materials, to obtain materials having uneven distribution of charges, wherein multilayer coating may occur in one spot, whereas other spots on the surface may be bare. Such products are acceptable in *filtration* processes due to the fact that the amount of impurities needed to be removed is relatively small compared to the bulk liquid volume, and that uneven charge distributions can be compensated by the depth of the filters. However, such products cannot readily be applied to delicate ion exchange processes. The number of active sites, as well as the accessibility of the active sites, are critical to the capacity of such process. The chemical functional groups in ion exchangers cannot be buried close to the surface, but have to be somewhat removed from the surface, possibly with a molecular side arm for accessibility. One way of achieving this has been through the incorporation into the fibrous matrix of silanes which are chemically modified. Such silanes may carry functional groups such as DEAE, CM or affinity chromatography sites. They are mechanically stable and strong and do not swell. However, they are expensive, and show very high non-specific adsorption of protein by the silica hydroxy groups.

In sum, neither the ion exchange or affinity chromatography supports commonly used in laboratory scale purifications, nor the particulate (or ion exchange modified particulate)-containing fibrous matrices for chromatography or filtration have proven to be of great use in scale-up of delicate purification processes.

A need therefore continues to exist for supports useful in industrial scale ion exchange and affinity chromatography purification processes, which will be noncompressible, controllably swellable, have high exchange capacity, exhibit high flow rates, be versatile and be relatively inexpensive to produce.

SUMMARY OF THE INVENTION

It is therefore an object of the invention to provide a novel molecular support.

Another object of the invention is to provide a molecular support useful for ion exchange chromatography, affinity chromatography or reverse phase chromatography.

Yet another object of the invention is to provide a chromatographic support useful for industrial scale chromatographic operations.

Still another object of the invention is to provide industrial processes of ion exchange, affinity chromatography, and reverse phase chromatography.

Yet another object of the invention is to provide processes for the preparation of ion exchange, affinity and reverse phase chromatographic supports.

These and other objects of the invention as will hereinafter become more readily apparent have been attained by providing:

A modified polysaccharide material, which comprises:
1. a polysaccharide covalently bonded to a synthetic polymer;
2. said synthetic polymer made from
   (a) a polymerizable compound which has a chemical group capable of being covalently coupled directly or indirectly to said polysaccharide; and
   (b) one or more polymerizable compounds containing (i) an ionizable chemical group, (ii) a chemical group capable of transformation to an ionizable chemical group, (iii) a chemical group capable of causing the covalent coupling of said polymerizable compound (b) to an affinity ligand or to a biologically active molecule, or (iv) a hydrophobic chemical group.

Another object of the invention has been attained by providing molecular separation materials derived from the aforementioned polysaccharide materials, capable of acting as chromatographic supports for ion exchange chromatography, for affinity chromatography, reverse phase chromatography or as reagents for biochemical reactors.

Still another object of the invention has been attained by providing molecular separation processes and/or biochemical reaction processes using the aforementioned materials.

BRIEF DESCRIPTION OF THE DRAWINGS

The present invention will become better understood by reference to the detailed description provided hereinafter when considered together with the accompanying drawings, wherein.

BRIEF DESCRIPTION OF THE PREFERRED EMBODIMENTS

Figure 1A:
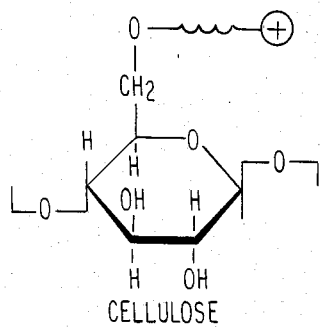
FIG. 1 is a diagram showing (A) an anion exchange cellulose derivatized by a prior art approach which yields one cationic site per saccharide unit and (b) an anion exchange cellulose derivatized by the approach of the invention which yields multiple cationic sites per saccharide unit.
Figure 1B:
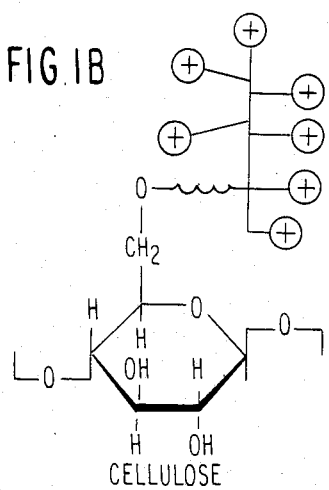
Figure 2:
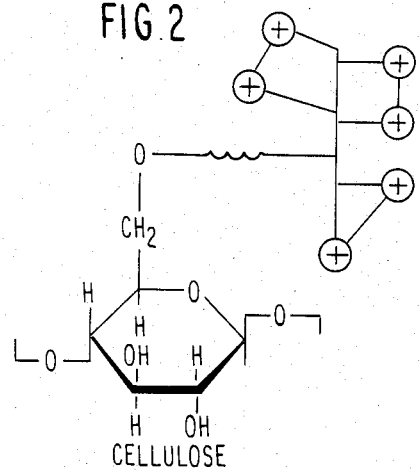
FIG. 2 shows the derivatized anion exchange cellulose of FIG. 1(B) after further crosslinking or quaternization.

The present invention is related to the discovery and development of materials useful as insoluble supports for a variety of application including a wide range of chromatographic separations, including affinity separations, or even as insoluble supports for bioreactors.

The support materials are based on a composite of an organic synthetic polymer and a polysaccharide. In its most used embodiment the composite per se is biologically inert. The organic synthetic polymer carries chemical groups which are capable of coupling to said polysaccharide, and also carries chemical groups which can provide ion exchange capacity, which can provide anchoring capacity for affinity ligands or for biologically active molecules in general.

Strictly speaking, the polymer coupled to the polysaccharide may be either a copolymer or a homopolymer. When the chemical groups capable of coupling to the polysaccharide are the same as the chemical groups useful as anchoring units for affinity ligands or biologically active molecules, the polymer, in this particular form would be a homopolymer. In the more general form, however, the polymer is a copolymer containing groups capable of coupling to the polysaccharide and also different groups capable of serving as anchoring groups for molecules.

The invention also relates to ion exchange materials obtained from the modified polysaccharide which are obtained by further reaction with crosslinking agents, and/or by further reactions such as chemical ionization, or unmasking of potentially masked ion exchange groups.

The invention also relates to materials derived from the modified polysaccharide by attaching thereto affinity ligands or biomolecules, to thereby obtain affinity chromatography or bioreactive materials, or attaching thereto hydrophobic substituents for reverse phase chromatography.

The invention also relates to mixtures of the aforementioned materials with unmodified polysaccharides, with modified or unmodified particulate material, or mixtures thereof to give a variety of separation media.

MATERIALS

The term "polysaccharide" as used in the specification and claims is meant to include compounds made up of many—hundreds or even thousands—monosaccharide units per molecule. These units are held together by glycoside linkages. Their molecular weights are normally higher than about 5,000 and up into the millions of daltons. They are normally naturally occurring polymers, such as, for example, starch, glycogen, cellulose, gum arabic, agar and chitin. The polysaccharide should have one or more reactive hydroxy groups. It may be straight or branched chain. The most useful of the polysaccharides for the purposes of this invention is cellulose.

The polysaccharide is preferably fully unprotected and carries all of its hydroxy groups in the free state. Some blocking of the hydroxy groups is possible, as for example by acylation or aminoacylation. Extensive blocking of the hydroxy groups of the polysaccharide, however, is undesirable since the polysaccharide thereby loses its hydrophilic character, which is necessary to provide appropriate chemically compatible interaction with biomolecules. If the polysaccharide becomes too hydrophobic, negative interactions with such molecules as proteins leads to possible non-specific bonding and denaturation phenomena. Also, if the masking of the polysaccharide hydroxy groups is too extensive, the reactivity of the resulting material with the polymer is greatly diminished. For all of these reasons, it is preferred to retain substantially all hydroxy groups in the free state. The polysaccharide may, however, be chemically activated, as seen infra.

Cellulose is the preferred polysaccharide. By "cellulose" is intended to mean any of the convenient and commercially available forms of cellulose such as wood pulp, cotton, hemp, ramie, or regenerated forms such as rayon. There exists no criticality as to the selection of a suitable form of cellulose. Cellulose is a naturally occurring polysaccharide consisting of $P(1\rightarrow4)$ linked glucose units. In the native state, adjacent cellulose chains are extensively hydrogen bonded forming microcrystalline regions. These regions are interspersed by amorphous regions with less hydrogen-bonding. Limited acid hydrolysis results in preferential loss of the amorphous regions and gives so-called microcrystalline cellulose. The cellulose useful in the present invention is either cellulose in the native state, or in the microcrystalline state. Also, cellulose derived from cotton linter is better than that derived from wood pulp, as the latter contains lignin.

Chemical reactions to attach the polymer to the polysaccharide material normally proceed with difficulty in crystalline regions but take place more readily in amorphous regions. For example, the substitution of functional groups into cellulose has a disruptive effect on the structure thereof. If carried out to completion, the cellulose matrix would be destroyed and ultimately water soluble polymers would be formed. Typical examples of this phenomenon are the hydroxyethyl cellulose and cellulose gums of the prior art, which becomes the commonly used adhesives and binders after dissolving in water.

Each anhydrous saccharide unit in a polysaccharide molecule may have three or more reactive hydroxy groups. Theoretically, all three or more can be substituted with the polymer. The product from such reaction, however, would have a degree of substitution of three or more, which in the case of ion exchange materials, would render it soluble. Even at levels of substitutions below those at which total water solubility occurs, such polysaccharide derivatives become unsuitable as chromatographic supports. Therefore, substitution of the polysaccharide is restricted to the more reactive centers of the amorphous regions and is seldom carried out beyond the level of about 1 mEQ/gm of dry weight in fiber form. At this level of substitution, the native configuration of the polysaccharide structure is only slightly modified, and the low density non-uniform exchange sites are readily accessible to large biomolecules.

The final structure of a molecular support of the invention thus comprises a polysaccharide chain covalently modified at a multiplicity of sites along such chain with the synthetic polymers.

The polymer which modifies the polysaccharide is either a homopolymer or a copolymer. The definition of the polymer as a homo- or copolymer depends on whether the polymerizable compounds (a) and (b) are different. In its most general form, the copolymer could be a random, a block or an alternating copolymer.

In one embodiment, the polymerizable compound (a) (also called "comonomer (a)") may have a group capable of reacting with a hydroxy group of polysaccharide with the formation of a covalent bond. Such polymerizable compounds are defined for example in U.S. Pat. No. 4,070,348 to Kraemer et al., which is herein incorporated by reference. The chemical groups are capable of reacting with hydroxy groups at temperatures up to those at which the polysaccharide begins to decompose or depolymerize, e.g., 0° to 120° C., in aqueous solution and thereby form covalent bonds with the oxygen atoms of the hydroxy groups. Since water is always present in considerable excess with respect to the hydroxy groups, chemical groups which react spontaneously with water, such as, for example, isocyanate groups, are less suitable. Aqueous solutions comprise pure water or mixtures of water with one or more water miscible co-solvents, such as alcohols, ketones, and the like.

Hydroxy reactive groups of comonomer (a) are preferably activated carboxy groups such as are known from peptide chemistry or O-alkylating agents, such as alkyl halide or epoxide groups. Representative of the O-alkylating comonomers are acrylic- and methacrylic anhydrides, acrylolylmethacryloyl N-hydroxy succinimides, omega-iodo-alkyl esters of acrylic or methacrylic acid in which the alkyl group in general contains 2 to 6 carbon atoms, allyl chloride, chloromethylstyrene, chloroacetoxy ethyl methacrylate, and compounds having a glycidyl group. The latter are ethers or esters formed between a glycidyl alcohol and an unsaturated alcohol or unsaturated carboxylic acid, respectively. The glycidyl alcohols are aliphatic and cycloaliphatic alcohols and ether alcohols having from 3 to 18 carbon atoms which are esterified with an alpha, beta-unsaturated carboxylic acid, preferably acrylic or methacrylic acid, or are etherified with an olefinically or acetylenically unsaturated alcohol. Typical compounds are glycidyl acrylate and methacrylate; 4,5-epoxy-pentylacrylate; 4-(2,3-epoxy-propyl)-N-butyl-methacrylate; 9,10-epoxystearylacrylate; 4-(2,3-epoxypropyl)-cyclohexyl methacrylate; ethylene glycol-monoglycidyl etheracrylate; and allyl glycidyl ether.

If the active monomer units (a) are sensitive to hydroxy groups, and if they do not react with the polysaccharide offered, they may be transformed, in the presence of water, into hydrophilic carboxy or hydroxy groups. The activated groups are therefore present in the polymeric material in generally greater number than is necessary for the bonding with the polysaccharide.

In another embodiment, the polymerizable compound (a) may be one which does not react directly with hydroxy groups of the polysaccharide, but rather is covalently coupled to the polysaccharide indirectly, via a bridge compound. This is the case when the polysaccharide is first chemically activated as by oxidation, and reacted with a compound having, e.g., an epoxy group or a vinyl group, capable of reaction with an appropriate functionality of polymerizable comonomer (a).

The polymerizable comonomer (b) will vary depending on the ultimate use of the carrier material. If the carrier material's ultimate use is to serve as an ion exchange chromatographic material, the comonomer (b) may contain any of the well known ionizable chemical groups or precursors thereof such as compounds containing a vinyl or vinylidene group and a carboxylic acid, a carboxylate salt, a carboxylate ester, preferably having 1 to 6 carbon atoms, a carboxylic acid amide, a secondary or a tertiary amine, a quaternary ammonium, a sulfonic acid, a sulfonic acid ester, a sulfonamide, a phosphoric or phosphonic acid, or a phosphoramide or phosphonamide group.

When comonomer (b) carries the precursor of a material having ion exchange properties, the ion exchangable group itself can be obtained by unmasking, such as for example, by selective hydrolysis of an anhydride, ester or amide, or salt formation with an appropriate mono-, di- or trivalent alkaline or alkaline earth metal, as is otherwise well known in the art.

Preferred ion exchange functionalities for comonomer (b) are aminoethyl, carboxymethyl, carboxyethyl, citrate, diethylaminoethyl, ecteola (mixed amines), guanido ethyl, phosphonic acid, p-aminobenzyl, polyethylene imine, sulphoethyl, sulphomethyl, triethylaminoethyl, or chelating groups such as —N(CH$_2$CO$_2$H)$_2$.

When the ultimate use of the carrier material is as a support for an affinity ligand, comonomer (b) carries a chemical group capable of causing the covalent coupling of said comonomer (b) to an affinity ligand, i.e. an "anchoring" group. Since most affinity ligands carry nucleophiles such as hydroxy, amino, thiol, carboxylate, and the like, any electrophilic group capable of reacting with such nucleophile can be present in comonomer (b). Such electrophilic groups include, but are not limited to, those described previously as active groups capable of reacting with the hydroxy group of cellulose. They also include activated carboxy groups used in peptide chemistry for the formation of peptide bonds, such as carbonyl chlorides, carboxylic anhydrides and carboxylic acid azide groups, as well as phenyl esters and aldehydes used for the formation of Schiff (imine) bases.

Also useful are the carboxylates of hydroxylamino derivatives of the formula (1)

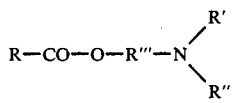

in which R is an alpha, beta-unsaturated, polymerizable radical and R' and R" are identical or different $C_1$-$C_6$ alkyl or alkanoyl groups. R''' may be a direct bond (—) or a $C_2$-$C_3$ alkyl group. R' and R" together with the N atom may also form a heterocyclic ring. Typical compounds of this type are:

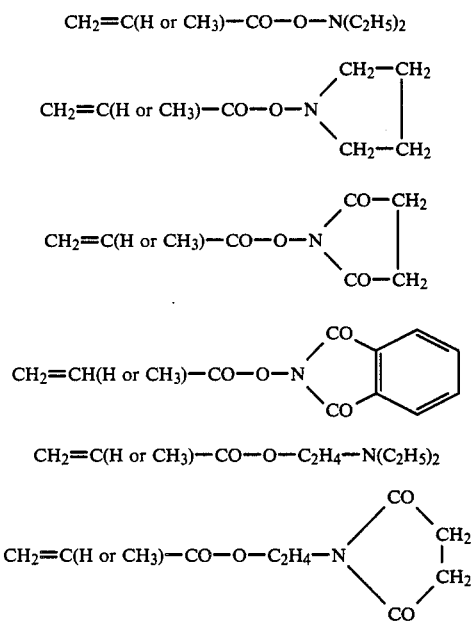

$$CH_2=C(H\ or\ CH_3)-CO-O-C_2H_4-N(C_2H_5)_2$$

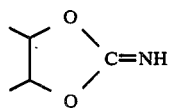

Other compounds having activated carboxyl groups include acryloyl- and methacryloyl chloride, acrylic and methacrylic anhydride, maleic anhydride, phenyl acrylate and methacrylate, glycidyl acrylate and methacrylate, 4-iodobutylacrylate and methacrylate and 2-isopropenyl-4,4-dimethyloxazolone-5. The last mentioned compound is capable of reacting with the terminal amino group of proteins.

A very useful potentially electrophilic reactive group in comonomer (b) useful for coupling to an affinity ligand is a group capable of being activated to an electrophilic group with a reagent such as a cyanogen halide. It is known in the art that cyanogen halides react with 1,2-diols to yield activated structures of the following type:

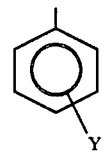

This structure is then capable of reacting with the nucleophile of an affinity ligand. Among the preferred 1,2-diols present in comonomer (B) are various saccharides, including monosaccharides such as glucose, mannose and galactose, disaccharides such as lactose and maltose, trisaccharides such as raffinose or, generally, glycosides. The 1,2-diol-containing functional group can be attached to the polymerizable comonomer (b) by such reactions as esterification, amide formation, esterification and the like. Among the most preferred of these is the reaction of glycidyl acrylate or methacrylate with a saccharide, to yield an ether-containing comonomer (b).

When the ultimate use of the carrier material is as a carrier for biological molecules, any of the anchoring groups mentioned for comonomers (a) or (b) can also be used. Other types of activated groups such as those containing aldehydes or amines can also be used.

The polymerizable comonomer (b) can be substantially of one type or can be a mixture of one or more types. This is particularly applicable when the ultimate use of the material is an an ion exchange carrier. Comonomers (b) can then contain such functional groups as anionic exchange groups and cationic exchange groups in various different ratios, if desired.

Preferably, the polymerizable monounsaturated compounds (b) are polymerizable compounds of the formula (4):

wherein
$R^1$ is hydrogen or methyl;
A is CO, or $SO_2$;
X is OH, OM (where M is a metal ion), $OR^2$ (where $R^2$ is a straight or branched chain $C_1$-$C_{18}$ alkyl group), $OR^3OH$ (where $R^3$ is a straight or branched chain $C_2$-$C_6$, alkyl or aromatic group), $NR^4R^5$ or $N^+R^4R^5R^6$ (where $R^4$ is the same or different as $R^5$ which is the same or different as $R^6$, and are hydrogen, $R^2$ or $R^3OH$);
AX may also have formula (5);

wherein Y is $-CO_2^-$, $-CH_2CO_2^-$, $-SO_3^-$, $-CH_2SO_3^-$, $-PO_4H^-$, $-CH_2PO_4H^-$, $-CH_2N(CH_2COO^-)_2$, $-CH_2-NR^4R^5$, or $-CH_2-N^+R^4R^5R^6$, or the corresponding free acid, ester or partial ester groups, as described previously. In these formulae, the groups $R^4$, $R^5$; $R^4$, $R^6$, or $R^5$, $R^6$ may form a 5-7 membered heterocyclic ring with the nitrogen atom. $R^4$, $R^5$, and $R^6$ are as previously defined.

Alternatively, (and when the material is to be used as an anchor for affinity ligands or biomolecules), A is CO or $SO_2$, and X is most preferably $O-CH_2-CH(OH)-CH_2-$Saccharide, where "—Saccharide" is a mono-, di- or polysaccharide having a group which can be activated for reaction with nucleophilic reactive groups on the affinity ligand or the biomolecule by a cyanogen halide.

The preferred comonomer (a) for anionic exchange materials is glycidyl acrylate or methacrylate. The preferred comonomer (b) for anionic exchange materials is diethylaminoethyl acrylate or methacrylate. The most preferred comonomer (b) for anchoring materials is the comonomer obtained from reaction of glycidyl acrylate or methacrylate with glucose.

The preferred comonomer (a) for cationic exchange materials is aminoethyl methacrylate, coupled to the polysaccharide by previous oxidation thereof. The preferred comonomer (b) for cationic exchange materials is methacrylic acid, acrylic acid and acrylic acid dimer, or glycidyl methacrylate further oxidized to a carboxylic acid group after copolymerization.

The average molecular weight of the polysaccharide-modifying polymer is dependent on the number of monomers present therein. It is required to have at least a sufficient number of comonomers (a) so as to be able to form covalent attachment throughout amorphous regions of the polysaccharide surface. The number of comonomers (b) cannot be too small, since otherwise the exchange capacity, or the anchoring/interlacing capacity is negligible. The number of comonomers (b) can neither be too high, since this would cause great difficulty in the reaction between the reactive groups of comonomer (a) and the polysaccharide. Preferably, the polysaccharide-modifying copolymer carries anywhere between 1 and 500 units (a) plus (b), most preferably between 20 and 100 units. This corresponds to molecular weights of between about 100 and 100,000, preferably between 1,000 and 10,000.

Other neutral comonomers (c), different than those represented by (i), (ii), (iii) or (iv) supra, can also be added to the polymer, if desired. These comonomers may be polymerizable unsaturated compounds carrying neutral chemical groups such as hydroxy groups, amide groups, alkyl groups, aryl groups and the like. Preferred among comonomers (c) are $C_1$-$C_6$ alkyl acrylates or methacrylates, or the corresponding hydroxy alkyl acrylates or alkacrylates. The function of comonomers (c) may be to increase the presence of hydrophobic or hydrophilic residues in the polymers, so as to provide a desired balance of hydrophilic and hydrophobic groups, if necessary.

The minimum ratio of comonomer (a) to total comonomer content is important. The synthetic polymer should have a sufficient amount of comonomer (a) to permit substantial covalent coupling of the polymer to the polysaccharide. If too little comonomer (a) is present in the polymer, then grafting becomes difficult, if not possible. Generally, about 4–12, preferably 5–10% by weight of comonomer (a) relative to the total of (a) plus (b) (and (c) if any is present) is needed. Amounts of about 0.5 to 1 or 2% by weight appear to merely crosslink the polymer, without substantial grafting onto the polysaccharide.

The upper limit of comonomer (a) in the polymer can be varied up to 99.9% by weight, depending on the desired amount of rigidity, functionality and hydrophilicity. Increasing the amount of comonomer (a) too much above 15 to 20% by weight, however, decreases the porosity. Large molecules then have difficulty in gaining full access to the functional groups in comonomer (b). It is preferred to have a predominance of comonomers (b) over comonomers (a). Comonomers (c) may be present in an amount of up to 20 percent by weight of the total (a) plus (b) plus (c).

The weight ratio of polysaccharide to the modifying polymer is freely adjustable, and varies from 0.1 to 5 weight part of copolymer to parts by weight of the polysaccharide.

When comonomers (b) carry ionizable chemical groups capable of providing cation exchange capacity, it is found that unless some degree of crosslinking is provided, the flexibility of the material in solution tends to favor the formation of micelle-type aggregates and slow loss of capacity. Therefore, it is a preferred mode of the invention to provide polymeric crosslinking for these types of modified polysaccharides. Crosslinking can be provided either by incorporating into the polymerization recipe a small amount of polyunsaturated comonomer having at least two polymerizable alpha, beta-carbon double bonds, such as for example mono- and polyethylene glycol dimethacrylates and diacrylates (with the polyethylene glycol residue containing up to 6 ethylene groups), ehtylene dimethacrylate, ethylene diacrylate, tetramethylene dimethacrylate, tetraethylene diacrylate, divinylbenzene, triallyl cyanurate, methylene-bis-acrylamide or -bis-methacrylamide, and the like.

Another type of crosslinking agent is particularly applicable to copolymers made from an aminoalkyl comonomer (b). Because of the presence of a free pair of electrons on the aminoalkyl nitrogen atoms, crosslinking can be carried out with such bifunctional reagents as would react with nitrogen free electron pairs. Among these are the diacyl halides, such as Hal—CO—(CH$_2$)$_n$—CO—Hal, or the alkyl dihalides, such as Hal—(CH$_2$)$_n$—Hal, wherein Hal is a halide such as chloride, bromide or iodide, and n may be anywhere between 2 and 12. Other bifunctional reagents capable of reaction with nitrogen atoms can also be used, including

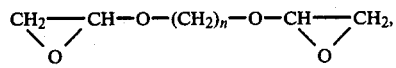

where n is 2-12. The advantage of these bifunctional reagents is that they simultaneously crosslink the copolymer, while also providing a cationic charge at the nitrogen centers, thereby ionizing the material.

The amount of crosslinking agent is best determined empirically. It is to be considered sufficient when the polymer preserves the ion exchange capacity at a constant value over time, yet would be too high if swelling is prevented, and too much rigidity is obtained in the final materials. Ideally, an amount of crosslinking agent between 5 to 20 mole percent of the synthetic polymer units is sufficient.

By the term "affinity ligand" is used throughout the present application and in the claims, is meant to include any small or high molecular weight molecule which can be immobilized in a stationary phase and used to purify a complementary binding molecule from a solute phase by affinity chromatography. For example, a ligand can be an inhibitor, a cofactor, a prosthetic group, or a polymer substrate, all of these useful to purify enzymes or holoenzymes. Other ligand/ligate pairs are enzyme/polymeric inhibitors; nucleic acid, single strand/nucleic acid, complementary strand; hapten or antigen/antibody; antibody/proteins or polysaccharides; monosaccharides or polysaccharides/lectins or receptors; lectins/glycoproteins or receptors; small target compounds/binding proteins; and binding protein/small target compounds. When antigen/antibody pairs are used as the ligand/ligate pair, the technique takes the particular name of "immunoaffinity" chromatography.

The "biologically active molecule" which can be bound to the carriers of the invention can include enzymes, enzyme substrates, inhibitors, hormones, antibiotics, antibodies, antigens, peptides, saccharides, nucleic acids, and the like. The only requirement for these molecules is that they have reactive groups thereon which can be covalently coupled to the anchoring chemical groups on comonomer (b).

Of particular interest is the immobilization of enzymes such a hydrolases, isomerases, proteases, amylases, and the like. These immobilized enzymes can then be used in biochemical reactors, as is otherwise well known in the art.

By the use of the term reverse phase chromatography or "hydrophobic interaction chromatography" is meant to include chromatography used to adsorb hydrophobic components in mixtures. Such components include lipids, cell fragments and the like. In this embodiment, comonomer (b) (iv) is usually an acrylate or methacrylate ester of $C_6$–$C_{18}$ straight or branched chain alcohols, or of aromatic alcohols such as phenol or naphthol.

The carrier materials of the present invention can be used per se in the same manner as other polysaccharide-based carrier materials of the prior art. Alternatively, and in a preferred mode, the polysaccharide material, which is preferably in fibrous form after the modification, can be formed into a self-supporting fibrous matrix, such as a fibrous sheet, with ion exchange properties, affinity chromatography properties, bioreactive or reverse phase properties. The modified fibrous polysaccharide fibrous media can also incorporate unmodified fibers of various different sizes, and, in addition, can also incorporate modified or unmodified particulate material.

The fibrous media comprises a porous matrix of fiber wherein, because of the nature of the present invention, the fiber is effective for molecular or ionic separations or molecular reactions. The matrix is substantially homogeneous with respect to each component. When a particulate is present, it is prefered to modify it so that it is also effective for molecular or ionic separations or reactions. Such a particulate should be contained in the fibrous phase in an effective amount to achieve the desired separations or reactions. The overall media is substantially inert and dimensionally stable.

The preferred particulates which can be used include all of those substances which can be provided in finely divided form and exhibit chromatographic functionality, i.e., capable of effective molecular separations and/or reactions. Mixtures of such compositions may also be utilized. Exemplary of such particulates are silica, alumina, zirconium oxide, diatomaceous earth, perlite, clays such as vermiculite, carbon such as activated carbon, modified polymer particulates such as other ion exchange resins, crystalline cellulose, molecular sieves, and the like, the surfaces of which may be modified in a conventional manner. Such materials are commercially available under a variety of trademarks such as Biosila, Hi-Flosil, Li Chroprep Si, Micropak Si, Nucleosil, Partisil, Porasil, Spherosil, Zorbax cil, Corasil, Pallosil, Zipax, Bondapak, LiChrosorb, Hypersil, Zorbax, Perisorb, Fractosil, Corning Porous Glass, Dowex, Amberlite resins, and the like.

Examples of references which describe particulates effective for molecular separations are Miller, U.S. Pat. No. 3,669,841, Kirkland et al., U.S. Pat. No. 3,722,181, Kirkland et al., U.S. Pat. No. 3,795,313, Regnier, U.S. Pat. No. 3,983,299, Chang, U.S. Pat. No. 4,029,583, Stehl, U.S. Pat. No. 3,664,967, Krekeler, U.S. Pat. No. 4,053,565 and Iher, U.S. Pat. No. 4,105,426. The entire disclosure of all of these references are incorporated by reference.

The particle size of the particulate is not critical but influences somewhat the flow rate at which the sample to be treated passes through the material. Usually, uniform particle sizes greater than about 5 microns are preferred, with about 10–100 microns constituting a practical operational range. The amount of the particulate can vary widely from about 10 wt. % up to 80 wt. % or more of the solid phase. The optimum particulate concentration will vary depending on the molecular separation desired.

The fibrous media should be capable of immobilizing the particulate contained therein, i.e., capable of preventing significant particulate loss from the stationary phase, yet having a porosity which enables the fluid to pass through the media. Thus, although the modified cellulose materials of the present invention are self-bonding and the additon of extra fibers or binders may not be necessary, it is possible to utilize such extra fibers or binders. Other fibers usable for the media include polyacrylonitrile fibers, nylon fibers, wool fibers, rayon fibers and polyvinyl chloride fibers, other cellulose fibers such as wood pulp and cotton, and cellulose acetate.

One embodiment of the invention is the provision of a fibrous media comprising two different types of celluloses: one a modified cellulose according to the invention and another an unmodified cellulose.

Another embodiment of the invention, which may also be coupled with the aforementioned celluloses is an unrefined structural fiber which assists in providing sheets of sufficient structural integrity in both the wet "as formed" condition, and in the final dry condition, and also allows handling during processing as well as suitability for the intended end use. Such fibers are typically relatively large, with commercially available diameters in the range of 6 to 60 micrometers. Wood pulp can also be used and has fiber diameters ranging from 15 to 25 micrometers, and fiber lengths of about 0.85 to about 6.5 mm. The unrefined self-bonding structural fibers typically have a Canadian Standard Freeness of +400 to +800 ml. These long self-bonding fibers may constitute greater than 50% of the fibrous media, by weight, preferably 60–100% of the fibrous media, and most preferably 100%. Optionally, a minor portion of cellulose pulp which has been refined to a Canadian Standard Freeness of between +100 and −600 ml may be incorporated with a major portion of the normally dimensioned cellulose pulp (+400 to +800 ml). In particular, from about 1 to about 20% of the refined pulp and about 50% to about 90% of the unrefined cellulose may be contained in the matrix. Particulate may also be added.

When the particulate materials are millimicron-sized, it may be desirable to use, in addition, a mixture of cationic and anionic resins as described by assignee's co-pending U.S. patent application Ser. No. 347,360, filed on Feb. 9, 1982. Alternatively, one may use a medium containing, in addition to the millimicron-sized particles, a neutral organic polymeric resin having oxygen atoms along the polymeric backbone thereof, as described in the assignee's co-pending U.S. patent application Ser. No. 401,361, filed on July 23, 1982.

Also of particular interest in the present invention is the use of modified cellulosic fibrous media carrying modified inorganic support materials, such as for example are described in Regnier, U.S. Pat. No. 3,983,299, Kirkland et al., U.S. Pat. Nos. 3,795,313, Kirkland et al., 3,722,181, Mazarguil et al., U.S. Pat. No. 4,034,139, Talley et al., U.S. Pat. No. 4,118,316, Ho Chang et al., U.S. Pat. No. 4,029,583 or Regnier, U.S. Pat. No. 4,108,603. These are all incorporated herein by reference. In particular, it is possible to derivatize siliceous particles with silanes and attach thereto various ion exchange or anchoring groups. In this embodiment then, both the cellulosic fiber and the siliceous particulate are modified, and their interaction provides increased anchoring and/or ion exchange capacity. The addition of particulate material tends to increase the rigidity and strength of the fibrous media and renders it readily useful for industrial applications, especially those involving high pressure.

PROCESSES OF PREPARATION

The polymer-modified polysaccharide material of the invention can be prepared in various modes. Generally speaking, in one mode, one can first prepare the polymer and then condense the same through its hydroxy reacting groups (if available) to the polysaccharide. Alternatively, in another mode, one can first react the polysaccharide with a hydroxy group-reactive comonomer (a) followed by copolymerization with comonomer (b) and any other comonomers (e.g., crosslinking comonomers, hydrophobic comonomers, etc.), as desired. These reactions are therefore of two types: (1) coupling of saccharides to hydroxy reactive groups on comonomer (a), and (2) polymerization of polymerizable unsaturated compounds. The order in which these are carried out is not particularly critical.

Still a third method of (indirectly) attaching the synthetic polymer to the polysaccharide involves previous chemical activation of the polysaccharide. For example, polysaccharide can be treated with oxidizing agents such as periodate, hydrogen peroxide, ceric or other metallic oxidizing ions or the like. Reaction of the activated polysaccharide with an amino-containing polymerizable monomeric compound followed by reduction, will normally yield derivatized polysaccharide-carrying unsaturated functionalities along the chain thereof. These unsaturated functionalities can then serve as further attachment positions for conjugating the polymer thereto.

Another type of chemical activation of the polysaccharide involves reaction with a compound such as a diepoxide or epichlorohydrin, which yields a derivatized polysaccharide-carrying epoxy or other groups along the chain thereof. These epoxy or other groups then serve as conjugating positions on the polysaccharide chains.

The chemical activation modes of (indirect) attachment of the polymer to polysaccharide are particularly useful when introducing negative (anionic) functionalities into the polymer. This is due to the fact that graft polymerization, which is a common way of conferring positive charge to polysaccharides such as cellulose, is not very effective when attempting to confer negative charges (present in carboxy, phosphoric, sulphonic groups, etc.) thereto.

Polymerization of comonomers can be carried out by radical chain, step-reaction, ionic and coordination polymerization. Particularly useful is radical polymerization.

The free radical addition polymerization of radical polymerizable comonomers is carreid out with free radical initiators using the well known steps of initiation, addition and termination. A usual procedure is to utilize a substance or substances which produce radicals capable of reacting with the monomers. Probably the simplest of all polymerization initiators are the organic peroxides and azo compounds. These substances decompose spontaneously into free radicals in common organic solvents at a finite rate, at temperatures between 50° and 140° C. For example, benzoyl peroxide decomposes into two benzoyloxy radical at 60° C. Another example is afforded by the azo compound azo-bis-isobutyronitrile which similarly decomposes into radicals at easily accessible temperatures.

The necessary energy may also be provided by irradiating the initiator system with ultraviolet light. For example, initiation can be provided by irradiating the initiator system in the presence of photo initiators such as benzophenone and its derivatives, benzoin alkyl ethers or derivatives, or acetophenone, with ultraviolet light. It is then necessary that the initiator molecules absorb in the spectral region supplied. In this way radicals can be generated at a finite rate at considerably lower temperatures than are necessary if purely thermal excitation is used. Finally, bimolecular reactions may produce radicals capable of initiating polymerization. Particularly important are the redox reactions, which occur in aqueous media, and involve electron transfer processes. For example, the systems Fe(II) plus hydrogen peroxide, or Ag(I), plus $S_2O_8^{--}$ are particularly important in initiating the radical polymerization of monomers. Because of the low temperature of initiation, the redox initiators or photochemically induced initiators are particularly preferred in the present invention. The amount of initiator is that sufficient to initiate the polymerization reaction. Polymerization is carried out until substantially all of the monomers or comonomers have been incorporated into the polymeric chains. This can be readily ascertained by simple analytical tests on the reaction mixture. Preferably, this polymerization is accomplished almost simultaneously with or immediately prior to the covalent coupling of the polymer to the polysaccharide. Preferably, the coupling and polymerization are performed in the same aqueous phase.

In one embodiment, the condensation of the comonomer (a) with the hydroxy group or groups of polysaccharide, whether carried out before polymerization or thereafter, is normally carried out by adjusting the temperature of the reaction mixture, or by adding an appropriate acid/base catalyst.

The most preferred method of carrying out the process is in a "one-pot" system, using a hydroxy reactive comonomer (a). All desired comonomers and polysaccharide are added to an inert solvent system, such as, e.g., water, alcohols, organics, and the like. The polysaccharide and comonomers are treated under conditions which will initiate polymerization of the comonomers. This can be accomplished, for example, by adding to a well stirred mixture a water solution of an initiator such as ammonium persulfate and sodium thiosulfate, and initiating polymerization from about 15° C. to 40° C. Alternatively, a photoliabile initiator can be added and initiation caused by photochemical means. After stirring for a time sufficient to allow the polymerization to proceed to completion, the linking of the formed copolymer to the hydroxy groups of polysaccharide is caused by increasing the temperature of the reaction mixture to a temperature sufficient to cause this condensation. In the case when the linking group on the copolymer is a glycidyl group, such temperature is normally around 80°–100° C. Reaction is then allowed to proceed at the second temperature for a time sufficient to either go to completion, or to achieve modification of the polysaccharide to the desired capacity. The product is filtered, washed and dried for further treatment, if necessary. Unreacted monomer is preferably washed away with alcohol, unreacted catalyst with aqueous media and polymer with methanol or ethanol.

Further reaction of the modified polysaccharide may be by crosslinking, activation of the ion exchange potential, as for example by quaternization of nitrogen functions, saponification of esters, ionization of acids, sulfonation, phosphorylation or oxidation of epoxides, or other similar procedures. Quaternization, saponification, oxidation and salt formation are reactions well known to those skilled in the art, and will not be described in greater detail. Needless to say, the reactions useful for potentiation of the ion exchange potential of the material should not destroy the polysaccharide/copolymer linkages. Generally, strong acid conditions should be avoided.

Quaternization of aminoalkyl functions can be carried out simultaneously with crosslinking by reacting the modified polysaccharide with diacyl halides or alkyl dihalides, at a ratio of 0.1 to 30 parts by weight of the halides per 100 parts of polysaccharide at appropriate temperature, time and solvent conditions.

Another further reaction of the modified polysaccharide materials would be to anchor the affinity ligands or biologically active molecules to the anchoring groups of comonomer (b). This reaction can be readily accomplished by mixing in an appropriate solvent, normally aqueous, the affinity ligand or biomolecule to be anchored and the modified polysaccharide, and carrying out anchoring for a time and under conditions sufficient to cause covalent coupling therebetween. It may be necessary to activate polysaccharide groups on comonomer (b) with such materials as cyanogen halides, and to then further treat the activated polysaccharides with the affinity ligands or biomolecules. In this embodiment, it is preferred to first couple the affinity ligand or biologically active molecule to comonomer units (b), and then bind the resulting polymer or copolymer to the polysaccharide.

The reactions between the affinity ligand or biologically active molecule and the anchoring groups on comonomer (b) are normally carried out at temperatures of from 0° C. to 50° C., and may involve the addition of catalysts such as acid or base, or metals, or such other materials as DCC. The resulting ligand- or biomolecule-containing modified polysaccharide is washed under appropriate conditions and is ready for further treatment, if necessary.

Hydrophobic comonomers (b) (iv) are normally added to a copolymerization mixture in the presence of alcoholic solvents and/or surfactants. Washing is then carried out with alcohols.

As an illustrative example of the formation of a product under this invention can be described a composite of (1) cellulose and (2) a copolymer of (a) glycidyl methacrylate (GMA) and (b) diethylaminoethyl methacrylate (DEAEMA). This will be used only to show the many variables which are involved in the preparation, and which can be controlled to achieve a virtually unlimited number of products and resulting properties.

Step 1. Fiber dispersion and addition of monomers

Cotton linter is dispersed in water at 1% solids content—DEAEMA and GMA are added.
Variables
   (A) Chemical nature and physical size of cotton;
   (B) Purity of monomer;
   (C) Percent solid content;
   (D) Monomer/cotton ratio;
   (E) DEAEMA/GMA ratio;

Step 2. Polymer Formation

Temperature of slurry is raised to 15° to 40° C., followed by addition of catalyst and reaction for 1–2 minutes.
Variables
   (A) Temperature and reaction time;
   (B) Amount of catalyst Step 3. Coupling of Polymers to Cotton Temperature of slurry is raised to 80° C. to 100° C. within 25 minutes. Surfactant is added.
Variables
   (A) Rate of temperature rise;
   (B) pH of slurry;
   (C) Surfactant effect Step 4. Wash (1)

Four volumes of water are used to wash the product in order to remove the inorganic catalyst left in the system.
Variables
   (A) Volume of water required to bring out the salt;
   (B) Mode of washing Step 5. Wash (2)

Two volumes of methanol are used to wash the product in order to remove the homopolymer and unreacted monomer.
Variable
   (A) Amounts of methanol, depending on reaction conditions Step 6. Wash (3)

Four volumes of water are used to wash the product in order to remove the methanol entrapped in the fibers.
Variable
   (A) Amount of water Step 7. Acidification The product from Step 6 is redispersed in water and 1M HCl is added gradually to pH 4.0–4.5.
Variable
   (A) Amount of water Step 8–14: Quaternization Step 8. Redispersal The product from Step 6 is redispersed in water to a 1% solids content.
Variable
   (A) Solids content Step 9. Quaternization 1,6 dichlorohexane is added to the slurry in the presence of KI as catalyst. The temperature is raised to 95° C. and refluxed for 15 hours.
Variables (A) Quaternization agent;
(B) Solvent;
(C) Reaction time and temperature Step 10. Wash (5)

Water is used to remove the KI salt and the quaternization agent.

Step 11. Wash (6)

Methanol is used to remove excess quaternizing agent by increasing its solubility.
Variable
  (A) Degree of washing Step 12. Wash (7)

A water wash is used to remove methanol from the system.

Step 13. Acidification

1M HCl is used to protonate remaining unquaternized DEAE.
Variable
  (A) Balanced DEAE and QAE depends on the degree of quaternization carried out in the system Step 14. Wash (8)

Excess acid is washed away.

The preferred formation of self-supporting fibrous media from the modified polysaccharide materials of the invention can be carried out immediately after polymerization and polysaccharide modification. In this mode, unmasking the ion exchange groups or anchoring of affinity ligands or biomolecules may be carried out on the formed sheets themselves. Alternatively, the fibrous media is formed after unmasking of the ion exchange groups and/or anchoring of affinity ligands or biomolecules. The preferred method is to form the fibrous sheets after polysaccharide modification, and carry out further reactions, such as unmasking and anchoring on the sheets.

A self-supporting fibrous matrix using the modified polysaccharide of the invention can preferably be made by vacuum filtering an aqueous slurry of fibers and, if desired, additional resins and modified or unmodified particulate. This forms a sheet having uniformly high porosity, fine pore-size structure with excellent flow characteristics and is substantially homogeneous with respect to fiber, resins and particulate.

The vacuum filtration is performed on a foraminous surface, normally a woven wire mesh which, in practice, may vary from 50 mesh to 200 mesh, with mesh openings ranging from 280 micrometers to 70 micrometers, respectively. Finer meshes are unsuitable because of clogging problems and/or structural inadequacy.

The sequence of adding the overall components to the slurry (modified fibers, other fibers, particulates, modified particulates, other resins, etc.) is relatively unimportant, provided that the slurry is subjected to controlled hydrodynamic shear forces during the mixing process. The slurry is normally prepared at, say, about 4% consistency and then diluted with additional water with a proper consistency required for vacuum filtering and sheet formation. This latter consistency will vary depending upon the type of equipment used to form the sheet. Typically, the slurry is cast onto a foraminous surface, vacuum filtered and dried in the conventional manner.

The flat, dimensionally stable sheet can be of any desired thickness and is then cut to the appropriate dimensions for each type of application. Preferably, the wet sheet is often dried and then cut to proper size in order to form discs. These discs can be loaded onto an appropriately sized cylindrical column to form the desired medium. The discs and cylinder should preferably be in interference fit so that the disc can be pushed into the cylinder without distortion, but not fall under gravitational force allowing gaps between the discs and the cylinder. After the column is packed dry, a pump can be used to pump solvent through the elements stacked in the column. Preferably, the elements swell to form a substantially tight edge seal to the cylinder wall. Because the individual elements are dimensionally stable, the column is not sensitive to orientation or handling, a problem which is common with other chromatographic media, particularly of any gel type media.

In a preferred embodiment, the modified polysaccharide media of the invention is fibrous form is shaped into a jelly-roll configuration, as disclosed in co-pending U.S. patent application Ser. No. 505,532 filed June 17, 1983 by Leeke et al., or in a configuration similar to that described for mechanical filtration in U.S. Pat. Nos. 2,539,767 and 2,539,768 to Anderson, and available from AMF, Incorporated, Cuno Division, as Micro-Klean ® Filter Cartridges, and described in a brochure of the same title, 1981, herein incorporated by reference.

The jelly roll configuration is normally shaped into a cartridge. Utilization of the cartridge has several advantages. Production scale flow rates of 200–500 ml/min can be utilized with the cartridge, depending on the application. The cartridges can be autoclaved separately by rolling/encasing in Kraft non-shedding paper. They can be housed in special housings made of polysulphone tubing with acetyl end caps, where the cartridge can be autoclaved. The cartridges show long term stability with respect to their binding capacities at room temperature storage.

The rigidity of the matrix allows the column to be operable in unrestricted diameter for high volume processes. The column volume is virtually unaffected by changing pH or ionic strength in the buffer solution. Such a system can be equilibrated and regenerated in a short period of time, eliminating cumbersome procedures of column preparation and regeneration.

USES

The ion exchange, affinity, reverse phase, or bioactive materials of the invention can be used in any of the well known prior art processes of ion exchange, affinity or reverse-phase chromatography, or as supports for bio-reactors.

The materials obtained in the present invention have unique properties over materials used heretofore. A binary system formed by mixing modified polysaccharide, e.g., cellulose, with other types of polysaccharide, such as microcrystalline cellulose, and forming a fibrous sheet (without the addition of extra particulate material) has the advantage of lacking silica materials, which normally shows nonspecific adsorption of proteins. A highly controllable degree of swelling which can be readily controlled by adjusting the multiple variables present in the system, allows the replacement of unmodified microcrystalline cellulose by other mechanical strengheners, has low production cost, and high exchange capacity or anchoring capacity, which can, in any event, be modified by controlling the ratio of comonomers (a) and (b).

A ternary system formed from modified polysaccharide, modified or unmodified particulate and unmodified fibers has the advantage of potential maximization of swelling, rigidity and capacity obtainable through varying the multiple variables present in the system. Flow rates can be controlled by varying the ratio of organic to particulate (especially silica) components without significant loss of capacity. In addition, such a system shows advantages over prior art systems using nonmodified celluloses in that, in many instances, no refined pulp is necessary, since the polymer linked on the polysacchride will function as well as refined pulp in bridging particles to the fiber surfaces. The polymeric components in the present system may also function as binder resins; therefore, addition of resins to the slurry can, if desired, be eliminated.

While ordinarily the prior art has relied on materials with high surface area to bind the maximum number of chemical groups thereon, the materials of the present invention provide means of binding multifunctional groups per each polysaccharide molecule. As long as these functional groups are made accessible for ion exchange or anchoring, the preparation is no longer limited to high surface area materials.

In protein separations and purifications, the key factor which ought to be avoided is possible damage to the protein molecules. In the present invention, this is avoided by using bicompatible materials such as polysaccharides with only limited amounts of organic polymers. The materials are swellable and provide for very little denaturation of protein. Nonspecific absorption of biopolymers is decreased, since both acrylic and saccharide polymers show very low amounts thereof, and are hydrophilic in nature.

Another area of design flexibility and design control is in the possible adjustment of the length of the acrylic polymer carrying the various ion exchange or anchoring groups. The variability of the polymer length not only may eliminate steric hindrance due to solute or ligand accessibility, but also minimizes leakage of the ligand from the matrix. The polymer "arm" should not be too long to avoid potential internal hydrophilic interaction, such as folding back. An "arm" of about 5 to 20 atoms is generally ideal for attaching the bioligands.

By the use of well known anchoring groups for affinity ligands or biomolecules, the materials can incorporate all of the synthetic methods developed in prior art commercial materials, such as Sephadex ® or Sepharose ®.

Finally, the matrix is chemically and physically stable with minimum change of dimensional stability upon contact with salt and eluents.

EXAMPLES

Having now generally described this invention, the same will be better understood by reference to certain specific examples which are included herein for purposes of illustration only, and are not intended to be limiting of the invention unless otherwise specified.

Example 1

Poly(diethylaminoethyl methacrylate)-g-Cellulose (a) Recipe

| Reagent | Quantity |
|---|---|
| Microcrystalline cellulose | 10 g |
| Diethylaminoethyl methacrylate | 25 cc |
| Glycidyl methacrylate | 2.5 cc |
| Ammonium persulfate | 1 g |
| Sodium thiosulfate | 1 g |
| Water | 500 cc |

(b) Procedure
1. Cellulose was well dispersed in water in a reactor.
2. Diethylaminoethyl methacrylate and glycidyl methacrylate were well mixed before pouring into the reactor.
3. After pouring the monomers into the reactor, the mixture was stirred for 5 minutes.
4. Ammonium persulfate and sodium thiosulfate were dissolved in 20 ml water; and then poured into the reactor.
5. The reactants were stirred for 20 minutes at 15° C. to 40° C.; the temperature was then increased to 80° C.
6. Stirring was maintained for 1 hour in the range of 80°–90° C.
7. A period of 0.5 hour was allowed to cool down the products.
8. The product was filtered and washed well with water and acetone.

(c) Results

The number of available DEAE functional groups was determined by titrating with 0.1M $HClO_4$ in glacial acetic acid (0.1M HCl in aqueous solution) on a Brinkman Potentiograph E 536. The instrument was calibrated by measuring commercial DEAE cellulose as the control, and capacity was expressed as milliequivalent (mEQ) per gram of dry material. The copolymerized cellulose showed approximately three times more capacity than that of the cellulose made from the conventional prior art derivative method.

The results were further confirmed by the measurement of albumin adsorption capacity. This was done by preparing a fibrous sheet, cutting into discs and packing in a 76 mm size column. Albumin in phosphate buffer solution was pumped through the column and later eluted with 1N NaCl solution. The amount of albumin measured at 280 nm O.D. showed the following results (Table 1):

TABLE 1

| | | Beaker Test on DEAE Media | | | | | |
|---|---|---|---|---|---|---|---|
| | | | pH | | | Capacity Test | |
| Sample No. | Sample Weight (Dry/Wet) | Media in Buffer | 0.1 M NaOH Added | Media In BSA | BSA Conc. | A280 t = 1 hr | (Mg/g) |
| 1 | 1/9.9 | 5.63 | 2.7 ml | 6.25 | 1030 mg | 0.25 | 991 |
| 2 | 1/8.7 | 5.5 | 3.2 | 6.25 | 1030 | 0.33 | 978 |
| 3 | 1/8.33 | 5.68 | 2.8 | 6.25 | 1025 | 0.38 | 966 |
| 4 | 1/7.69 | 5.68 | 2.8 | 6.25 | 1025 | 0.69 | 918 |

TABLE 1-continued

| | | Beaker Test on DEAE Media | | | | Capacity Test | |
|---|---|---|---|---|---|---|---|
| | | pH | | | | | |
| Sample No. | Sample Weight (Dry/Wet) | Media in Buffer | 0.1 M NaOH Added | Media In BSA | BSA Conc. | A280 t = 1 hr | (Mg/g) |
| 5 | 1/7.69 | 5.68 | 2.8 | 6.25 | 1895 | 4.5 | 1195 |
| 6 | 1/8.7 | 5.57 | 3.9 | 6.30 | 1025 | 0.19 | 995 |
| 7 | 0.88/8.0 | 5.5 | 3.6 | 6.30 | 1533 | 1.49 | 1298 |
| 8 | 1.0/8.33 | 5.52 | 3.3 | 6.25 | 1030 | 0.36 | 974 |
| 9 | 1.0/8.33 | 5.52 | 3.3 | 6.25 | 1236 | 0.97 | 1085 |

Example 2

Quaternized Poly(diethylaminoethyl methacrylate)-g-Cellulose (a) Recipe

| Reagent | Quantity |
|---|---|
| Poly(diethylaminoethyl methacrylate)-g-cellulose (Example 1) | 5 g |
| 1,6-Dichlorohexane or 1,4 dichlorobutane | 3 cc |
| Potassium iodide | 0.1 g |
| Isopropanol | 100 cc |
| Water | 100 cc |

(b) Procedure

1. A round neck flask was filled with wet poly(diethylaminoethyl methacrylate)-g-cellulose, 1,4 dichloroburane, potassium iodide and isopropanol.
2. The reaction mixture was refluxed overnight.
3. The product was filtered and washed well with acetone and water.
4. The sample was acidified with $10^{-2}$N HCl, then washed well with water.

(c) Results

The results demonstrate the effectiveness of 1,6-dichlorohexane as cross-linker on fixing the charged groups. 1,6-dibromo or diiodo hexane have also been applied as cross-linkers with success.

To improve quaternization percentage, water soluble quaternization reagents, also compounds, such as 1,3-dichloro-2-propanol, 1-chloro-2-propanol, chloroacetic acid, methyl chloroacetate and chloroethyl diethylamine can be applied with success. The quaternized (QAE) media derived from ethyl iodide showed exceptionally high BSA binding capacity in the pH range from 7 to 8.5. The results are shown in Tables 2 and 3.

TABLE 2

Quaternization Percentage in QAE Media Derived from Different Q-Reagents

| Sample No. | Q-reagent | Q (%) |
|---|---|---|
| QAE-1 | 1-chloro-2-propanol | 13 |
| QAE-2 | 1,2-dichloro-2-propanol | 77 |
| QAE-3 | methyl chloroacetate | 83 |
| QAE-4 | chloroethyldiethylamine | 82 |
| QAE-5 | ethyl iodide | 80 |

TABLE 3

BSA Capacity of Various QAE Media vs. pH of Phosphate Buffer Solution

| Sample No. | Q-reagent | BSA Cap. (Mg/g) | pH | BSA Cap. (Mg/g) | pH | BSA Cap. (Mg/g) | pH |
|---|---|---|---|---|---|---|---|
| QAE-1 | methyl chloroacetate | 1527 | 6.29 | 1027 | 7.36 | 758 | 8.69 |
| QAE-2 | 1-chloro-2-propanol | 1376 | 6.30 | 671 | 7.30 | 336 | 8.12 |
| QAE-3 | 1,2-dichloro-2-propanol | 1466 | 6.25 | 676 | 7.29 | 387 | 8.18 |
| QAE-4 | ethyl iodide | 1391 | 6.27 | 1015 | 7.59 | 816 | 8.26 |
| QAE-5 | 1-chloro-2,3-propanediol | 1397 | 6.28 | 692 | 7.33 | 367 | 7.98 |
| QAE-6 | chloroethyl diethylamine | 1483 | 6.27 | 559 | 7.39 | 290 | 8.60 |
| DEAE | — | 1625 | 6.38 | 738 | 7.32 | 296 | 7.98 |

Example 4

A beaker test on the capacity of media prepared according to Sample 7 of Table 1 supra was carried out on various different types of protein molecules. The results are shown in Table 4 below:

TABLE 4

| | | Beaker Test on Media | | | | Capacity Test | |
|---|---|---|---|---|---|---|---|
| | | pH | | | | | |
| Sample No. | Sample Nature (Dry/Wet) | Media in Buffer | 0.1 M NaOH Added | Media in Protein | Protein Conc. | A280 t1 = hr | (Mg/g) |
| 1 | Ovalbumin PI = 4.6 crude dried egg white m.w. = 43,000 50 mg/ml | 5.74 | 5.0 ml | 6.3 | 2038 | 4.37 | 1343 |
| 2 | BSA PI = 4.9 (50 mg/ml m.w. = 65,000) | 5.63 | 4.0 | 6.3 | 1811 | 3.07 | 1327 |
| 3 | Soybean PI = 4.15 Trypsin m.w. = 20,100 Inhibitor (10 mg/ml) | 5.52 | 5.0 | 6.3 | 443 | 1.55 | 200 |
| 4 | Amylo- PI = 3.5 glucosidase (20 mg/ml) | 5.60 | 4.1 | 6.3 | 954 | 4.25 | 282 |

TABLE 4-continued

| Sample No. | Sample Nature (Dry/Wet) | Beaker Test on Media | | | | Capacity Test |
|---|---|---|---|---|---|---|
| | | pH | | | | A280 |
| | | Media in Buffer | 0.1 M NaOH Added | Media in Protein | Protein Conc. | t1 = hr (Mg/g) |
| 5 | Pepsin PI = 2.2 (50 mg/ml) m.w. = 34,500 | 5.63 | 3.9 | 6.3 | 1744 | 2.52  1073 |

Example 5
Plasma Fractionation Using the Media of Example 2

775 ml of Cohn fractions II and III from human plasma were dissolved in 0.01M phosphate buffer at pH 6.5 This solution was added at a column (7.7 cm i.d.×4.3 cm length, vol=200 ml) containing 25 g of the media of Example 2. 2.7 g of IgG were recovered from the non-bound fractions whereas elution of bound material with 1M sodium chloride yielded 7.5 g of albumin.

Example 6
Formulation of a Sheet Containing both Modified Cellulose and Modified Silica (a) Silanization of Silica The silanization process can be performed either in toluene or in water. The reaction mechanism involves condensation of the halide or silanol functional grups on the organo-silane with silanols on the silica surface. Therefore, the reaction conditions depend very much on the nature of the silane and the surface property of silica. The selection of silica is made based on both chemical and physical factors. Chemically, it should have a surface property favorable for silanization reactions; physically, the particle size should be large enough to permit the least amount of pressure build-up in a column up to 2 ft. length as long as the composite structure homogeneity can be maintained in the formulation. The following three grades of silica gel from Davidson Chemicals are the choice to meet such requirements:

| Grade | Approx. Particle Size (Micron) | Surface Area (m²/g) | Pore Vol. (cc/g) | Pore Dia. A | pH 5% Slurry |
|---|---|---|---|---|---|
| 922 | 50 | 750 | 0.43 | 22 | 4.0 |
| 950 | 30 | 600 | 0.43 | 25 | 6.0 |
| 952 | 70 | 320 | 1.50 | 250 | 7.0 |

The maximum pore diameter from Davidson's product is around 250 A, which can only accommodate protein molecules smaller than albumin. Controlled pore glass of 1000 A or controlled pore silica of 500 A needs to be used to facilitate the diffusion of larger protein molecules such as IgG or immune complex. DEAE or SP are introduced onto silica gel through the following route:

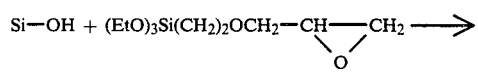

HOC$_2$H$_4$NH$_2$ or HOC$_2$H$_4$N(C$_2$H$_5$)$_2$

-continued

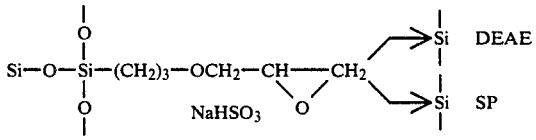

(b) Formulation of the Slurry

The modified cellulosic fiber from Example 2 and the silanized silica from (a) were mixed in a tank at 1 to 2% consistency to form a slurry according to the following formulations (Table 5):

TABLE 5

| Sample No. | Modified (Long Cellulosic) Fiber (%) | Refined Pulp (+40 CSF) % | DEAE on Silica 952 % | % Retention |
|---|---|---|---|---|
| 1 | 20 | 10 | 70 | 90 |
| 2 | 30 | 0 | 70 | 80 |
| 3 | 30 | 20 | 50 | 95 |
| 4 | 50 | 0 | 50 | 90 |
| 5 | 20 | 7% (+40) & 7% (−10) | 60 | 100 |

Alternatively, copolymerization can be performed on the mixture of large and small refined pulp in the same reactor. Silica 952, being large in size (70 micron or larger), can be held by the modified cellulose alone without refined pulp. No binder is require, since the polymer on cellulose is also functional as a binder.

(c) Formation of a Column

The slurry was cast onto a foraminous surface, vacuum felted, an dried in a conventional manner. The flat, dimensionally stable sheet was then cut to the appropriate dimensions for each type of column. The cut discs were stacked in the cylinder in an appropriate height.

(d) Discussion and Results

The above prepared matrix was cut to 9.0 mm diameter sized discs and stacked to 6-inch length with 0.85 grams of dry weight material. After following the swelling, adsorption and elution procedures, the albumin adsorption capacity was measured and the number of DEAE groups was titrated, with the results shown in the following Table 6:

TABLE 6

| Exp No. | Matrix Characterization | | | Capacity | |
|---|---|---|---|---|---|
| | Modified | +40 Refined Pulp | Silica 952 | By Titration (mEQ/G) | Albumin Adsorption (mg/g) |
| 1 | 20% (Inact.) | 10% (Inact.) | 70% (Act.) | 0.89 | 171 182 |
| 2 | Act. | — | Act. | 2.0 | 245 249 |
| 3 | Act. | — | Inact. | 1.0 | 120 123 |
| 4 | Inact. | Inact. | Inact. | 0 | 0 |
| 5 | 100% | — | — | 2.0 | 264 |

TABLE 6-continued

| | Matrix Characterization | | Capacity | |
|---|---|---|---|---|
| Exp No. | +40 Refined Modified Pulp | Silica 952 | By Titration (mEQ/G) | Albumin Adsorption (mg/g) |
| | Act. | | | 270 |

The results fully demonstrate the contribution of the ion exchange functional groups from the organic matrix. The enhanced capacity is achieved by making cellulose and binders all contributing their available sites for ion exchange, in addition to silica.

Example 7

Preparation of an Affinity Chromatography System

Component A: cellulosic fiber
Component B: glycidyl methacrylate
Component C: glucose

Method A

Step 1. Coupling of C to B

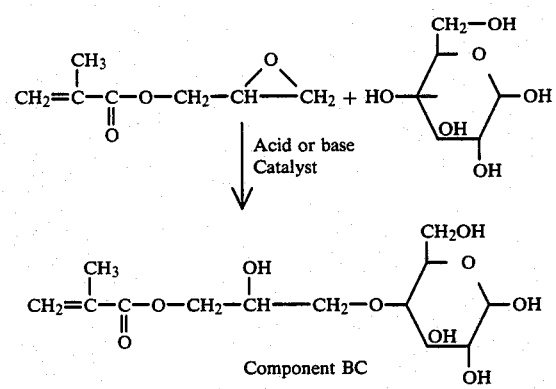

Step 2. Formation of Polymers with Controlled Ratio of B to BC

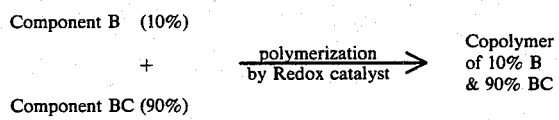

Step 3. Coupling of the Above Copolymer to Component A

With excess amount of catalyst left in Step 2, the epoxy groups in Component B of the above copolymer can be coupled to cellulose, by raising the temperature to 90° C. The chemical reaction is exactly the same as Step 1, except that the Component A is in polymeric form whereas Component C is a monomer.

Method B

Step 1. Formation of Acrylic Copolymer

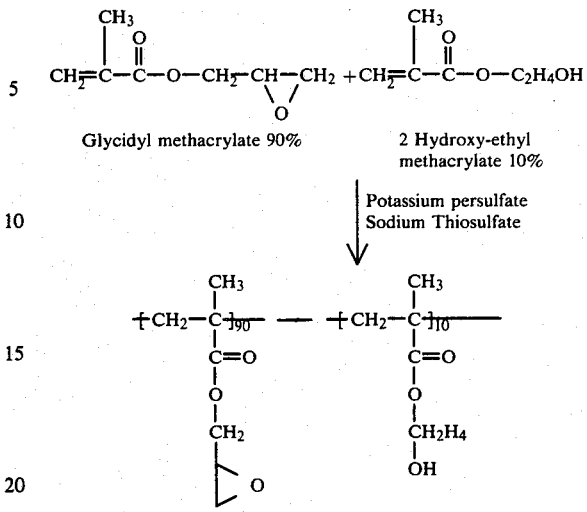

Step 2. P Component C is added to the polymer on a proper molar ratio such that 90% of the available epoxy groups will be reacted with C under acid or base catalytic conditions. The remaining 10% will be left available for coupling on to the cellulose surface afterwards.

Example 8

Formation of an Anionically Modified Cellulose According to the Invention

1. Cellulose Activation

Cellulose was reacted with potassium periodate in 2-5% water dispersion, with the periodate being at 2% w/v at pH 3.0 for about 2 hours at room temperature (or 30 min at 40° C.) while stirring constantly. The oxidized cellulose was vacuum felted on a screen and washed with deionized water until removal of the unreacted oxidants was complete. The conductivity of the washing water was measured until no more salt came off from cellulose.

2. Monomer Coupling to the Activated Cellulose

The activated cellulose was redispersed in deionized water at 2% consistency, and amino ethyl methacrylate (AEM) was added. The weight ratio of AEM to cellulose was approximately 25%. The temperature was raised to 50° C. and AEM was allowed to react with the activated cellulose for 1 hour under agitation.

3. Formation of Copolymers

Glycidyl methacrylate (GMA) was then added at a weight ratio of 9 to 1 AEM, while maintaining the reactor at 50° C. Nitrogen gas was bubbled into the reaction tank to remove oxygen gas dissolved in the aqueous system. Catalyst, such as ammonium persulfate and sodium thiosulfate mixture or organic peroxide, was added to initiate the polymerization reaction via the vinyl groups for 10 minutes. The reaction kinetics could be followed by measuring the solution turbidity or the decrease of glycidyl groups in the liquid.

4. Conversion of the Glycidyl Groups to the Corresponding Anionic Groups

The conversion of epoxy groups to carboxyl groups was performed by using potassium permangnate as oxidant at 60° C. for 4 hours. The final product was thoroughly washed with deionized water and methanol for removing unreacted species and homopolymers.

5. Fabrication of Chromatographic Columns

The materials thus prepared were formulated by vacuum felting to form composite filter pads as shown in Table 7.

extinction coefficient of BGG being =1.3, the capacity was expressed as follows:

TABLE 7

FORMULATION OF ANIONICALLY MODIFIED PADS

| FILTER NO. | NATURAL CELLULOSIC FIBER Soft Cotton Linter[1] | POLYMER GRAFTED ON FIBER | | POLYMER GRAFTED ON M.C.[2] POWDER CELLULOSE | | BINDER RESIN Ethylene Glycol Diglycidyl Ether |
|---|---|---|---|---|---|---|
| | | TYPE Cotton Linter with GMA | Wt. of polymer/ wt. of Fiber | TYPE M.C. of 90 micron size[3] | Wt. of polymer/ Wt. of M.C. | |
| Cat #1 | 15% | 40% | 2.0 | 40% | 1.0 | 5% |
| Cat #2 | 20% | 40% | 1.5 | 35% | 0.5 | 5% |
| Cat #3 | 10% | 50% | 1.0 | 35% | 0.5 | 5% |

[1]Southern Cellulose Co.
[2]M.C. = microcrystalline.
[3]From FMC, Grade pH 102.

The balance of pad capacity and flow rate can be adjusted, based upon the following reaction variables.
(a) Size of cotton fibers and microcrystalline cellulose powder,
(b) The amount of polymers grafted onto cellulose,
(c) The structure and nature of the polymers,
(d) The nature and the amount of the oven-dried sheets can be cut into proper sizes and can be stacked into columns for chromatographic separation of protein molecules.

Capacity Test Results

The capacity of a column with this material was measured from the amount of bovine gamma globulin (BGG) adsorbed on the column under specific conditions, and was expressed as milligrams of BGG adsorbed per gram of column material. The procedure of the test was as follows:

(a)
A perstaltic pump was connected to the column with a pressure gauge installed in the line and a UV monitoring unit, to follow the protein concentration at 280 NM.

(b) Column Packing
A column packed with 25 mm dia disks and 6-inch in height will generally have pressure across the column in the range of 1 to 10 PSI, depending on the flow rate and pad porosity. The pads should be packed snugly so there is very little gap between them but not jammed with great force to fragment their structure. The total amount of pads installed in the column was weighed so the total capacity could be expressed either on the column volume or on a weight basis.

(c) Column Equilibration
The equilibrium buffer was pumped through the column until the effluent had the same pH and conductivity as the starting solution. About 5 volumes of buffer were needed to reach the equilibrium conditions.

(e) Adsorption of BGG by the Cationic Exchange Column

Based on an average BGG adsorption capacity around 200 mg/g of pad, a volume of BGG solution was poured into a granulated cylinder so that there were about two volumes of the amount of BGG required to saturate the column. The solution was recycled through the column at 5 ml/min of flow. The concentration of BGG was monitored by the UV monitor at 280 nm. When the column reached the saturation point, the $A_{280}$ leveled off. The column was washed with equilibration buffer until $A_{280}$ returned to baseline. With the $$\frac{\text{capacity of BGG adsorbed}}{\text{gram of pad}} = \left(\frac{A_{280} \times \text{total volume}}{1.3}\right) \text{ divided by total weight of the pad}$$

The pH effect on the capacity of the cationic exchange filter No. Cat. #1 and Cat. #2 are shown in Table 8.

TABLE 8

| Pad Weight | Column Size | pH | Adsorption Condition Flow Rate | WP | Capacity on BSA Mg/g |
|---|---|---|---|---|---|
| 3.29 g | 25 mm × 7 pads | 5.5 | 2 ml/min | 8 | 837 |
| 3.29 g | 25 mm × 7 pads | 6.0 | 2 ml/min | 8 | 960 |
| 2.21 g | 25 mm × 4 pads | 6.5 | 2 ml/min | 0 | 665 |
| 2.03 g | 25 mm × 4 pads | 7.0 | 2 ml/min | 1 | 530 |
| 2.11 g | 25 mm × 4 pads | 7.5 | 2 ml/min | 0 | 215 |

Conclusions for Example 8

A cationic exchanger with high capacity has been developed, as tested by adsorption of Bovine gamma globulin. High flow rate applicable for large scale industrial operations can be attained.

The system is basically a composite structure with cellulose fiber as supporting backbone and an acrylic polymer carrying glycidyl groups covalently linked to the backbone. These groups are converted to corresponding anionic functional groups through various types of oxidation.

As long as the lignin content is kept low, the reaction between cellulose and the polymer will proceed according to the conditions covered in this Example.

Example 9

Cellulose Grafted with Polymethacrylic Acid (a) Recipe

| Reagent | Quantity |
|---|---|
| Cotton linter fiber | 36 g |
| Methacrylic acid (or β-carboxyethyl acrylate) | 90 ml |
| Glycidyl Methacrylate | 9 ml |
| Triton X-100 | 54 g |
| Sodium Lauryl Sulfate | 1.5 g |
| Ammonium persulfate | 9.8 g |
| Sodium Thiosulfate | 9.8 g |
| Tributyl Amine | 1.0 ml |

(b) Procedure
1. Disperse 36 g of cotton linter fiber in 2 liters of water and add Tributyl Amine.
2. Add mixed surfactants: nonionic Triton X-100 (from Rohm & Haas) and Sodium Lauryl Sulfate (from Alcolac).
3. Add mixed monomers: methacrylic acid and glycidyl methacrylate, and raise temperature to 40° C.
4. Add catalyst mixture: ammonium persulfate and sodium thiosulfate pre-dissolved in water.
5. Raise temperature to 80° C. for 1 hour under strong agitation.
6. Let the reaction cool to room temperature, and wash with 4 columns de-ionized of water.
7. Wash with methyl alcohol once, and again wash with water to remove alcohol.
8. Adjust the pH by adding 0.1M alkaline solution.

(c) Results

The capacity test conducted by the beaker method by contacting positively charged protein molecules with the media of this example give the following results:

TABLE 9

| Protein Molecules Adsorbed | pH of Solution and Buffer Nature | Capacity |
| --- | --- | --- |
| Bovine Gamma globulin | pH = 6.5 in Acetate buffer | 300 mg/g |
| Hemoglobin | pH = 6.5 in Acetate buffer | 700 |
| Lysozyme | pH = 7.4 in 0.01 M Phosphate buffer | 750 |
| Bovine Serum albumin | pH = 4.6 in Acetate buffer | 85 mg/g |

Having now fully described this invention, it will be understood by those skilled in the art that the same can be performed within a wide and equivalent range of parameters, conditions, structures and uses without effecting the spirit or scope of the invention as of any embodiment thereof.

Examples 10-14

These examples show the use of the carrier of the invention in a fibrous matrix shaped into a jelly-roll form and in cartridge configuration.

Example 10

Separation of Protein Mixtures by DEAE Cartridges

In this example, it is demonstrated that DEAE "jelly-roll" cartridges, like columns, can be utilized to separate protein mixtures with a high degree of resolution. Unlike columns, the cartridges have no undesirable pressure problems and can therefore be operated at a high flow rate with a low pressure drop. In fact, out of 15 cartridges tested, all units gave reproducible and comparable results.

Experiment A shows the separation of an artificial mixture by bovine γ-globulin and bovine albumin. Experiment B shows the fractionation of human plasma. Cartridges (diameter 2.5 cm, height 7.5 cm) were used in both of these experiments.

Experiment A

Protein: A mixture of two subclasses of γ-globulin (483 mg) and bovine serum albumin (432 mg)
Buffers:
  Buffer A: Phosphate buffer (0.01M) at pH=6.8
  Buffer B: Phosphate buffer (0.05M) at pH=6.0
  Buffer C: Phosphate buffer (0.05M) at pH=6.2+1M NaCl 282 mg-globulin Type I (100% pure) was eluted with 1M NaCl in Buffer A (Peak A in FIG. 3).

Figure 3:
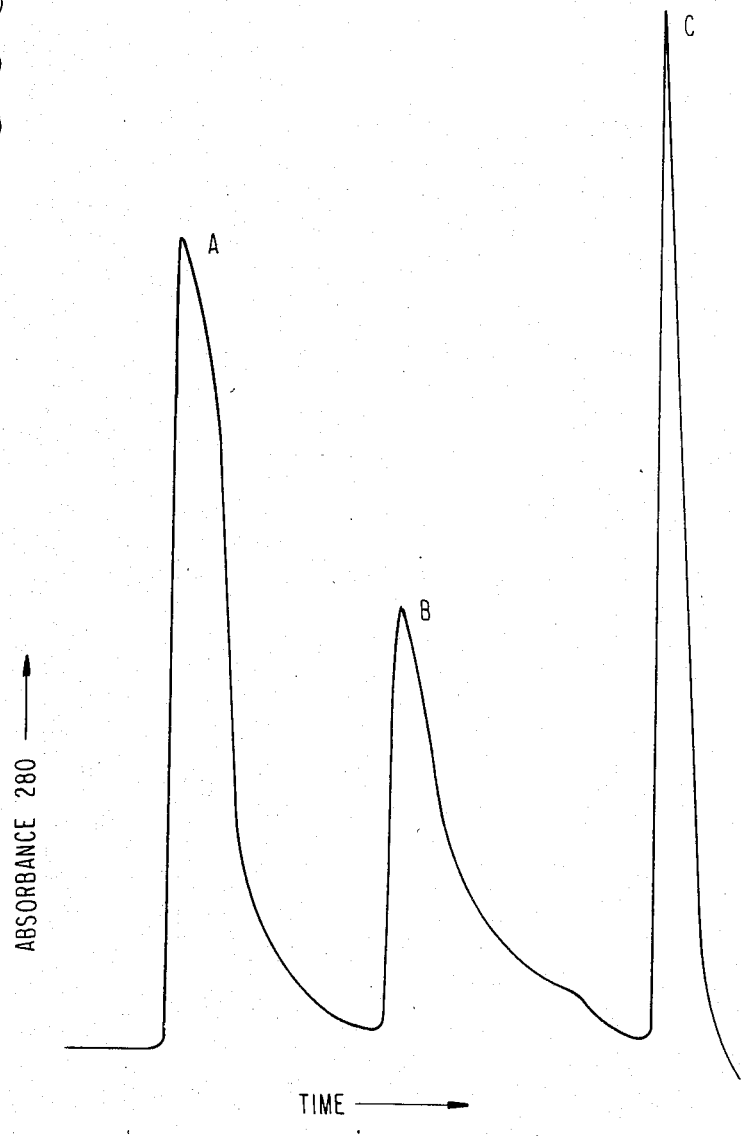
FIG. 3 shows the separation of gamma globulin type I (A), gamma globulin type II (B), and albumin (C), as per Example 10.

148 mg-globulin Type II (approximately 90% purity) was eluted in Buffer B (Peak B in FIG. 3).

Albumin (95%) purity) was eluted in Buffer C (Peak C in FIG. 3).

Experiment B

Protein: 10 mL plasma, pH=6.8 (adjusted pH)
  Gradient elution: 0.01M phosphate buffer (pH=6.8 to 4.5)
  Peak I: γ-globulin
  Peak II: Transferrin
  Peak III: Albumin
  Electrophoretic studies indicate that the fractions are at least 90% pure.

Yield and Recovery

Protein applied:

| 10 mL plasma total O.D.$_{280}$ = | 390 |
| --- | --- |
| γ-globulin O.D.$_{280}$ = | 59.4 |
| Transferrin, O.D.$_{280}$ = | 44.0 |
| Albumin, O.D.$_{280}$ = | 163.0 |
| Other eluted proteins = | 84.06 |
|  | 350.46 |
| Yield = 88% | |

Example 11

Elution Bound Transferrin by pH Shift Using DEAE Cartridge

DEAE ("jelly-roll") cartridge media reduces protein binding capacities at a more alkaline pH than 7.0. This unique pH shift has been utilized to elute bound proteins at higher pH without the use of salts and subsequent dialysis or ultrafiltration.

Figure 4:
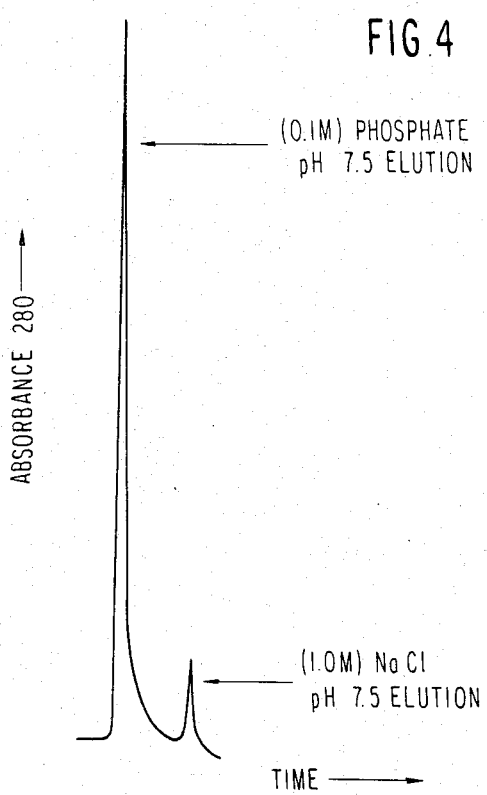
FIG. 4 shows results obtained in the elution of bound transferrin by pH shift using a DEAE cartridge, as per Example 11.

A previous study had shown that 85.4% bound BSA was eluted with (0.1M) phosphate at pH 7.5. In the present example, a similar observation was found with transferrin. Transferrin was bound to a DEAE cartridge media with a (0.01M) phosphate buffer at pH=6.8, and eluted with (0.01M) phosphate, pH=7.5. 92% bound transferrin was eluted in one column volume. The remaining transferrin was eluted with (0.1M) phosphate pH=7.5 and (1M) NaCl. FIG. 4 shows the results.

Example 12

Use of DEAE and CM Cartridges for IgG Fractionation

1. DEAE Cartridge ("Jelly-Roll")
  Applied Protein: Dialysed human plasma
  Binding Conditions: Phosphate Buffer (0.01M: 0.9–1.2 mS) pH=6.3
  Elution Conditions (continuous or step is usable):

|  | [Buffer] | Conductivity | pH |
| --- | --- | --- | --- |
| IgG | 0.01 M | 1.0 mS | 6.8 |
| Transferrin | 0.025 M | 1.75 mS | 6.04 |
| Albumin | 0.06 M | 3.85 mS | 5.14 |

2. CM Cartridge ("Jelly-Roll")

Applied Protein: Unbound IgG from previous DEAE step
Binding Conditions: Phosphate Buffer (0.01M: 0.9-1.2 mS) pH=6.0
Elution Conditions:

|  | [Buffer] | pH | [Salt] |
|---|---|---|---|
| IgG | 0.05 M | 6.3 | 1 M |

Example 13

CM Cartridge Capacity at Different pH Values

Figure 5:
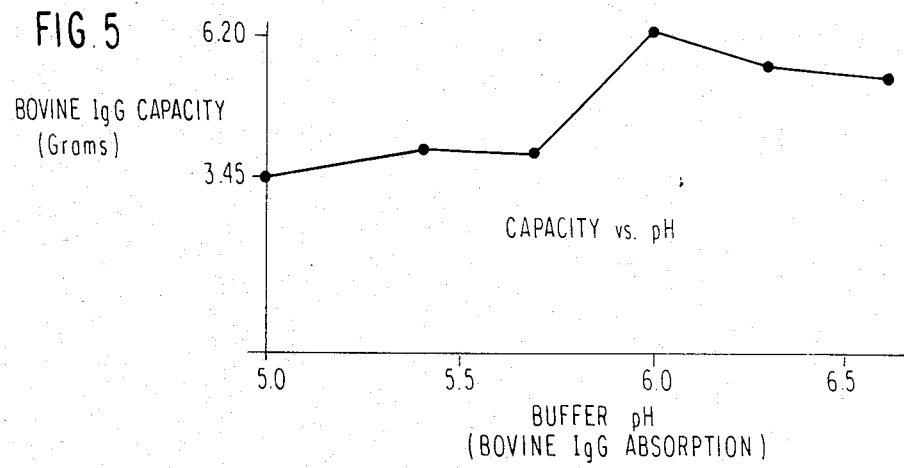
FIG. 5 shows the adsorption capacities for bovine IgG at various pH's as per Example 13.

Comparative Studies were made with a CM Cartride ("jelly-roll") and commercial Whatman ® CM-52. Details are shown on FIG. 5 and Tables 10 and 11.

TABLE 10

| | Invention Cartridge | | |
|---|---|---|---|
| Buffer pH | Elution Condition | Cartridge Bovine IgG Capacity | Recovery (%) |
| Phosphate (0.01 M) pH = 6.6 | Phosphate (0.05 M) pH = 6.3 (1 M) NaCl | 5.43 g | 94 |
| Phosphate (0.01 M) pH = 6.3 | Phosphate (0.05 M) pH = 6.3 (1 M) NaCl | 5.96 g | 96 |
| Phosphate (0.01 M) pH = 6.0 | Phosphate (0.05 M) pH = 6.3 (1 M) NaCl | 6.2 g | 100 |
| Phosphate (0.01 M) pH = 5.7 | Phosphate (0.05 M) pH = 6.3 (1 M) NaCl | 3.8 g | 99 |
| Acetate (0.02 M) pH = 5.4 | Acetate (0.2 M) pH = 4.0 (1 M) NaCl | 3.9 g | 100 |
| Acetate (0.02 M) pH = 5.0 | Acetate (0.2 M) pH = 4.0 (1 M) NaCl | 3.45 g | 98 |

TABLE 11

| | | Whatman CM-52 ® | | | |
|---|---|---|---|---|---|
| Buffer pH | Nature of Matrix | Column Dimension | Adsorption Condition | Elution Condition | Bovine IgG Capacity (mg/g) | Recovery (%) |
| Phosphate (0.01 M) pH = 6.5 | Microgranules preswollen | (a) 21 mL (b) 16 mm (dia.) | 2 mL/min. | Phosphate (0.05 M) (1 M) NaCl | 1.71 g | 42 |
| Phosphate (0.01 M) pH = 6.0 | Microgranules preswollen | (a) 21.5 mL (b) 16 mm (dia.) | 2 mL/min. | Phosphate (0.05 M) (1 M) NaCl | 4.48 g | 89 |
| Phosphate (0.01 M) pH = 5.5 | Microgranules preswollen | (a) 22 mL (b) 16 mm (dia.) | 2 mL/min. | Phosphate (0.05 M) (1 M) NaCl | 7.8 g | 87.6 |

Example 14

Plasma Fractionation Using Quaternized Media Cartridges

Figure 6:
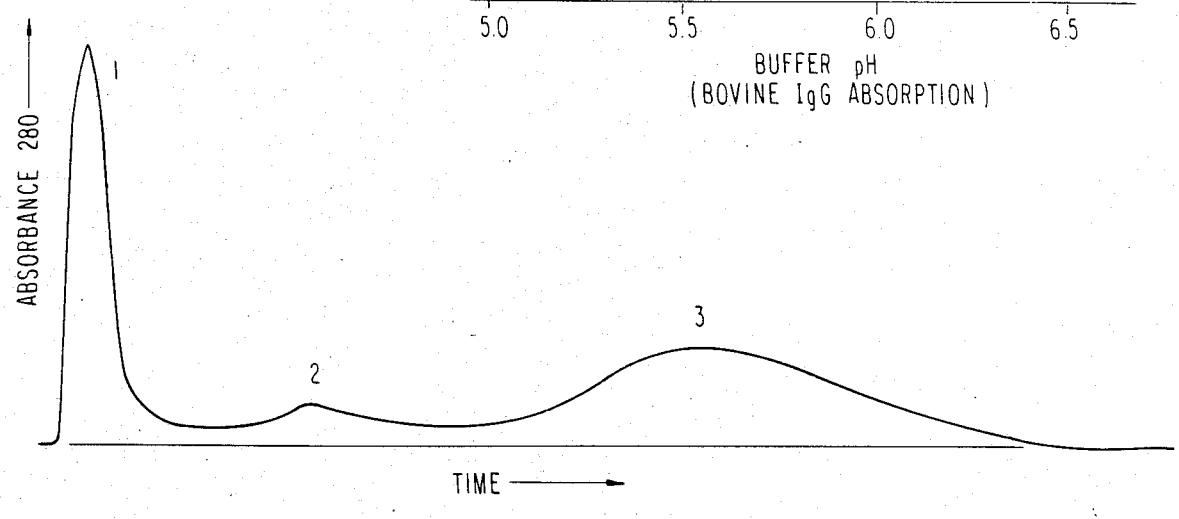
FIG. 6 shows plasma fractionation using a quaternized cartridge medium as per Example 14.

Cartridge dimensions: 2.5 cm (dia.)×7.5 cm (height)
Protein: 10 mL plasma, pH=6.8
Gradient: Continuous phosphate buffer (0.01M), pH=7.3 to (0.2M), pH=4.5
Material
Input: 10 mL plasma, total O.D.$_{280}$=400
Output: Total O.D.$_{280}$=377; Yield: 94.25%
Results are shown on FIG. 6.

Example 15

Invention Media Containing Hydrophobic Groups (a) Recipe

| Reagent | Quantity |
|---|---|
| Refined pulp (+260) | 20 g |
| n-octyl acrylate | 50 ml |
| Glycidyl methacrylate | 5 ml |
| Ammonium persulfate | 2 g |
| Sodium thiosulfate | 2 g |
| Water | 933 cc |

(b) Procedure

1. Refined pulp (+260) was well dispersed in water in a 3 neck, 3 liter round flask.
2. n-Octyl acrylate and glycidyl methacrylate were well mixed before pouring into the reactor.
3. After pouring monomers into the reactor and mixing the reaction mixture well, ammonium persulfate and sodium thiosulfate solutions were charged into the reactor at room temperature.
4. The reaction mixture was strongly agitated and the reaction temperature was raised to 82° C. within 15 minutes.
5. Stirring was maintained for 1 hour in the temperature range of 80°-85° C.
6. After cooling down the reaction mixture, the product was washed well with water.

Example 16

Invention Media Containing Chelating Groups

Poly(3-N,N-dicarboxymethyl-2-hydroxy-propyl methacrylate)-g-cellulose (a) Recipe

| Reagent | Quantity |
|---|---|
| Refined pulp (+260) | 50 g |
| Glycidyl methacrylate | 12.5 cc |
| Ammonium persulfate | 0.5 g |
| Sodium thiosulfate | 0.5 g |
| Sodium iminodiacetate | 2 g |
| Water | 250 cc |

(b) Procedure

1. Refined pulp (+260) was well dispersed in in 800 cc water in a 3 neck reactor.
2. After pouring glycidyl methacrylate into the reactor and mixing the reaction mixture well, ammonium persulfate and sodium thiosulfate were charged into the reactor at room temperature.

3. The reaction mixture was strongly agitated, and the reaction temperature was raised to 80° C. within 15 minutes.
4. Stirring was maintained for 1 hour in the temperature range of 80°-85° C.
5. The reaction mixture was cooled to 60° C., and then sodium iminodiacetate was charged into the reactor. Further reaction was continued for 26 hours.
6. The reaction mixture was cooled, and product was filtered and washed.

Example 17

Effect of Polymer Composition of Protein Adsorption Capacity

| Exp. No. | Polymer Composition % GMA as Coupler | % DEAEMA as Functional Groups | Method of Polymer Formation | BSA Adsorption Capacity mg/g media |
|---|---|---|---|---|
| 1 | 16% | 84% | *10% Surfactant | 650 |
| 2 | 14 | 86 | " | 854 |
| 3 | 12 | 88 | " | 1,106 |
| 4 | 10 | 90 | " | 1,446 |
| 5 | 8 | 92 | " | 1,548 |
| 6 | 6 | 94 | " | 1,620 |
| 7 | 4 | 96 | " | 972 |
| 8 | 2 | 98 | " | 280 |
| 9 | 83 | 91.7% | Without Surfactant | 980 |
| 10 | 10 | 90 | Without Surfactant | 1,450 |
| 11 | 12.5 | 87.5 | Without Surfactant | 1,650 |

*10% surfactant (Lauryl Alcohol Ethoxylate) on the basis of cellulose weight forms latex type polymer.

The results indicate that either increasing or decreasing the GMA composition too much beyond the range of 4 to 12% by weight decreases the adsorption capacity. Values of GMA higher than about 12% cause a decrease in porosity, whereas values lower than about 4% cause losses in grafting efficiency.

What is claimed as new and desired to be secured by Letters Patent of the United States is:

1. A modified polysaccharide material which comprises:
   (1) a water insoluble polysaccharide covalently bonded to a synthetic polymer
   (2) said synthetic polymer comprising a copolymer made from a free-radical polymerization of
      (a) a polymerizable compound containing an epoxy group capable of direct covalent coupling to a hydroxy group of said polysaccharide and a vinyl group, capable of free-radical polymerization; and
      (b) a polymerizable compound having the formula

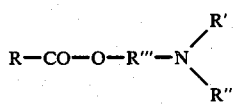

wherein R is an alpha, beta-unsaturated polymerizable radical, R' and R" are the same or different $C_1$-$C_6$ alkyl or alkanoyl groups, and R''' is a direct bond or a $C_2$-$C_3$ alkyl group, wherein R' and R" taken together with the N atom may form a heterocyclic ring.

2. The material of claim 1 wherein said polysaccharide is cellulose.

3. The material of claim 1 wherein the amount of said compound (a) in said synthetic polymer is sufficient to cause substantial covalent coupling of the polymer to said polysaccharide, yet insufficient to cause substantial loss of porosity of the modified polysaccharide.

4. The material of claim 3 wherein said polymer contains more of said compound (b) than of said compound (a).

5. The material of claim 4 wherein the ratio of said compound (b) to said compound (a) is about 88–96% by weight of (b) to 4–12% by weight of (a).

6. The material of claim 1 wherein said polymer is crosslinked and said crosslinking is provided by means of bifunctional reagents capable of reacting with at least two nitrogen atoms of said polymerizable compound (b) per reagent.

7. The material of claim 6 wherein said reagent is

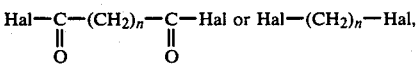

where Hal is a halogen atom, or

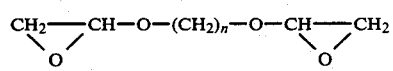

and n is 2 to 12.

8. A self-supporting cellulosic fibrous matrix which comprises the material of claim 1.

9. The matrix of claim 8 which also comprises highly refined cellulose pulp with a Canadian Standard Freeness of between +100 to −600 ml.

10. The matrix of claim 8 which also comprises a particulate material.

11. The matrix of claim 8 which is in the form of a sheet.

12. A process for preparing the modified polysaccharide material of claim 1 which comprises:
   (1) polymerizing said compound (a), with said compound (b) in the presence of said polysaccharide, under temperature conditions insufficient to cause the covalent binding of said compound (a) to said polysaccharide, to thereby form a synthetic polymer of (a) and (b); and
   (2) reacting said polysaccharide with the chemical group of compound (a) in said synthetic polymer under temperature conditions sufficient to cause said covalent bonding.

13. The process of claim 12 wherein said step (2) is carried out at a temperature which is higher than that used for step (1).

14. The process of claim 12 wherein said compound (a) carries nitrogen atom-containing groups and which further comprises the step of cross-linking said synthetic polymer with a bifunctional cross-linking reagent capable of reacting with at least two nitrogen atoms per reagent.

15. A chromatography column for effecting chromatographic separation of at least two components of a sample flowing therethrough comprising:

at least one solid stationary phase, said phase having chromatographic functionality and being effective for chromatographic separation;

a means for distributing the sample through the stationary phase;

wherein the stationary phase comprises:

(a) a plurality of layers of sheets of swellable fibrous matrix having chromatographic functionality and being effective for chromatographic separation; and (b) a spacer means between each layer for permitting controlled swelling thereof and enhancing the distribution of sample flowing through the stationary phase, and further wherein the swellable fibrous matrix in sheet form comprises a modified cellulose material, said modified cellulose material comprising the material of claim 2.

16. A modified polysaccharide material according to claim 1, wherein said synthetic polymer comprises a copolymer of diethylaminoethyl methacrylate and glycidyl methacrylate.

17. The modified polysaccharide material of claim 1 wherein said copolymer is quaternized with a quaternizing agent selected from the group consisting of 1-chloro-2-propanol; 1,2,-dichloro-2-propanol; methyl chloroacetate; chloroethyldiethylamine; and ethyl iodide.

18. The modified polysaccharide material of claim 1 wherein compound (a) is selected from the group consisting of glycidyl acrylate, glycidyl methacrylate, 4,5 epoxypentylacrylate, 4-(2,3)-epoxypropyl-N-butyl-methacrylate, 9,10-epoxysteoryl acrylate, 4-(2,3-epoxypropyl)-cyclohexyl methacrylate, allyl glycidyl ether and ethylene glycol-monoglycidyl-etheracrylate.

19. The process of claim 56 wherein said bifunctional cross-linking agent is selected from

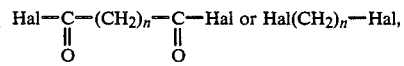

where Hal is halogen atom, or

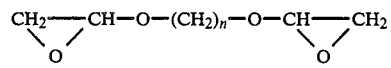

and n is 2 to 12.

20. A method of fractionating plasma comprising passing said plasma through the chromatographic column of claim 15.

21. The method of claim 20 wherein the synthetic polymer is a copolymer of dimethylaminoethyl methacrylate and glydicyl methacrylate.

22. A process for effecting chromatographic separation of at least two components of a sample comprising contacting said sample with a self-supporting fibrous matrix comprising a modified polysaccharide material, said modified polysaccharide material comprising:

(1) a water insoluble polysaccharide covalently bonded to a synthetic polymer;

(2) said synthetic polymer comprising a copolymer made from a free-radical polymerization of (a) a polymerizable compound containing an epoxy group capable of direct covalent coupling to a hydroxy group of said polysaccharide and a vinyl group, capable of free-radical polymerization; and (b) a polymerizable compound having the formula

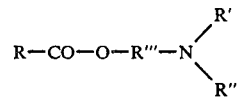

wherein R is an alpha, beta-ethylenically unsaturated polymerizable radical, R' and R" are the same or different $C_1$-$C_6$ alkyl or alkanoyl groups, and R''' is a direct bond or a $C_2$-$C_3$ alkyl group, wherein R' and R", taken together with the N atom may form a heterocyclic ring.

23. The process of claim 22, wherein compound (a) is selected from the group consisting of glycidyl acrylate, glycidyl methacrylate, 4,5 epoxypentylacrylate, 4-(2,3)-epoxypropyl-N-butyl-methacrylate, 9,10-epoxysteoryl acrylate, 4-(2,3-epoxypropyl)-cyclohexyl methacrylate, allyl glycidyl ether and ethylene glycol-monoglycidyl-etheracrylate.

24. The process according to claim 22, wherein said synthetic polymer comprises a copolymer of diethylaminoethyl methacrylate and glycidyl methacrylate.

25. The process according to claim 24, wherein said copolymer of glycidyl methacrylate and diethylaminoethyl methacrylate is in its quaternized form.

26. The process according to claim 25, wherein said copolymer is quaternized with a quaternizing agent selected from the group consisting of 1-chloro-2-propanol; 1,2,-dichloro-2-propanol; methyl chloroacetate; chloroethyldiethylamine; and ethyl iodide.

* * * * *